(12) United States Patent
Doi

(10) Patent No.: US 9,079,229 B2
(45) Date of Patent: Jul. 14, 2015

(54) **MICROORGANISM BELONGING TO GENUS *BACILLUS*, THROMBOLYTIC ENZYME, AND METHOD FOR TREATING WASTE**

(71) Applicant: Microbial Chemistry Research Foundation, Tokyo (JP)

(72) Inventor: Hiroyasu Doi, Tokyo (JP)

(73) Assignee: MICROBIAL CHEMISTRY RESEARCH FOUNDATION, Tokyo (JP)

(*) Notice: Subject to any disclaimer, the term of this patent is extended or adjusted under 35 U.S.C. 154(b) by 232 days.

(21) Appl. No.: 13/828,078

(22) Filed: Mar. 14, 2013

(65) Prior Publication Data

US 2013/0196415 A1   Aug. 1, 2013

Related U.S. Application Data

(63) Continuation of application No. PCT/JP2011/071724, filed on Sep. 22, 2011.

(30) Foreign Application Priority Data

Sep. 24, 2010   (JP) .................. 2010-214271

(51) Int. Cl.
    *C02F 3/34*    (2006.01)
    *C12N 9/54*    (2006.01)
    *B09B 3/00*    (2006.01)
    *C12R 1/125*   (2006.01)
    *B09B 5/00*    (2006.01)

(52) U.S. Cl.
    CPC ... *B09B 3/00* (2013.01); *B09B 5/00* (2013.01); *C02F 3/341* (2013.01); *C12N 9/54* (2013.01); *C12R 1/125* (2013.01); *C12Y 304/21062* (2013.01); *C02F 3/342* (2013.01)

(58) Field of Classification Search
None
See application file for complete search history.

(56) References Cited

U.S. PATENT DOCUMENTS 8,420,074 B2 * 4/2013 Rehberger et al. ......... 424/93.45

FOREIGN PATENT DOCUMENTS

| JP | 11-179327 | 7/1999 |
|---|---|---|
| JP | 11-244833 | 9/1999 |
| JP | 2000-005738 | 1/2000 |
| JP | 2000-262276 A | 9/2000 |
| JP | 2001-095564 | 4/2001 |
| JP | 2001-198566 | 7/2001 |
| JP | 2001-300505 | 10/2001 |
| JP | 2002-136952 | 5/2002 |
| JP | 2003-053303 | 2/2003 |
| JP | 2003-145196 | 5/2003 |
| JP | 2004-057209 | 2/2004 |
| JP | 2004-073906 | 3/2004 |
| JP | 2004-122118 A | 4/2004 |
| JP | 2007-189906 A | 8/2007 |
| JP | 2010-011866 | 1/2010 |

OTHER PUBLICATIONS

Milner, M. and Makise, K. "Natto and Its Active Ingredient Nattokinase: A potent and Safe Thrombolytic Agent" Alternative & Complementary Therapy, Jun. 2002, pp. 157-164.*
UniProt "P35935" Nattokinase sequence, deposited Jun. 1, 1994, UniProt database, 2 pages.*
Office Action mailed by the Japanese Patent Office on Aug. 19, 2014, for corresponding Patent Application No. JP 2012-535086, 4 pages.
Office Action mailed by the Japanese Patent Office on Aug. 19, 2014, for corresponding Patent Application No. JP 2012-535086. (English Translation), 5 pages.
Fujita et al., "Purification and Characterization of a strong Fibrinolytic Enzyme (Nattokinase) in the Vegetable Cheese Natto, a popular soybean fermented food in Japan", Biochemical and Biophysical Research Communications, Dec. 30 1993, pp. 1340-1347, vol. 197—issue No. 3.
T. Imai et al., "Study of the Jellyfish Decomposition by Enzyme", Thermal and Nuclear Power Engineering, Jul. 2009, pp. 636-640, vol. 60—issue No. 7.
T. Imai et al., "Study of the Jellyfish Decomposition by Enzyme", Thermal and Nuclear Power Engineering, Jul. 2009, pp. 636 to 640, vol. 60—issue No. 7. (English Translation).
Yin et al., "Bioproperties of Potent Nattokinase from *Bacillus subtilis* YJ1", J. Agric. Food Chem., May 12, 2010, pp. 5737-5742, vol. 58—issue No. 9, American Chemical Society.
Chang et al., "Potent Fibrinolytic Enzyme from a Mutant of *Bacillus subtilis* IMR-NK1", J. Agric. Food Chem., 2000, pp. 3210-3216, vol. 48—issue No. 8, American Chemical Society.
Doi et al., "Decomposition of Jellyfish by Thrombolytic Enzyme produced by Microorganism 104-1-3-1 Strain belonging to the genus *Bacillus*", Proceedings of Meeting of Japanese Society for Marine Biotechnology, May 28, 2011, p. 89, vol. 14.
Doi et al., "Decomposition of Jellyfish by Thrombolytic Enzyme produced by Microorganism 104-1-3-1 Strain belonging to the genus *Bacillus*", Proceedings of Meeting of Japanese Society for Marine Biotechnology, May 28, 2011, p. 89, vol. 14. (English Translation).
Doi et al., "Removal of CODMn from Jellyfish Wastewater by Bioreactor Using Microorganisms", Bulletin of the Society Sea Water Science, 2007, pp. 342-351, vol. 61—issue No. 6, Japan.
Doi et al., "Mass Jellyfish decomposition system by enzyme", Bioscience & Industry, 2008, pp. 627-629, vol. 66—issue No. 11.
Doi et al., "Mass Jellyfish decomposition system by enzyme", Bioscience & Industry, 2008, pp. 627-629, vol. 66—issue No. 11, (English Translation of p. 627 section 1, 1 page).

(Continued)

*Primary Examiner* — Rosanne Kosson
*Assistant Examiner* — Aaron J Kosar
(74) *Attorney, Agent, or Firm* — Pergament Gilman & Cepeda LLP; Milagros A. Cepeda; Edward D. Pergament

(57) ABSTRACT

A microorganism belonging to the genus *Bacillus*, wherein the microorganism belonging to the genus *Bacillus* is any one of a *Bacillus subtilis* 104-1-3-1 strain (Accession No: NITE BP-680) and a derivative strain thereof, and wherein the microorganism belonging to the genus *Bacillus* produces a thrombolytic enzyme which decomposes waste.

6 Claims, 14 Drawing Sheets

(56) References Cited

OTHER PUBLICATIONS

Doi et al., "Application of protease isolated from an actinomycete for *Nemopilema nomurai* Kishinouye decomposition", Nippon Suisan Gakkaishi, 2008, pp. 784-795, vol. 74—issue No. 5.
International Search Report dated, Dec. 13, 2011 for corresponding International Patent Application No. PCT/JP2011/071724, 4 pages.
Extended European Search Report dated Sep. 23, 2014, for corresponding European Patent Application No. EP 11 82 6928, 7 pages.
Wang and Yeh, "Purification and characterization of chitosanase from the nattokinase producing strain *Bacillus subtilis* TKU007", Process Biochemistry, 2007, pp. 132-138, vol. 43, Elsevier Ltd.
Hsu et al., "Amyloid-Degrading Ability of Nattokinase from *Bacillus subtilis* Natto", Journal of Agricultural and Food Chemistry, 2009, pp. 503-508, vol. 57, American Chemical Society.

* cited by examiner

MICROORGANISM BELONGING TO GENUS *BACILLUS*, THROMBOLYTIC ENZYME, AND METHOD FOR TREATING WASTE

CROSS-REFERENCE TO RELATED APPLICATION

This is a continuation application of PCT/JP2011/071724, filed on Sep. 22, 2011, which claims priority to Japanese Patent Application No. 2010-214271 filed on Sep. 24, 2010; all of which are hereby incorporated by reference in their entirety.

BACKGROUND OF THE INVENTION

1. Field of the Invention

The present invention relates to a microorganism belonging to the genus *Bacillus*, which produces a thrombolytic enzyme decomposing waste, a thrombolytic enzyme produced by the microorganism belonging to the genus *Bacillus*, and a method for treating waste using the thrombolytic enzyme.

2. Description of the Related Art

Seaside plant facilities such as power plants or steel plants require large amounts of cooling water and employ seawater as the cooling water. These facilities are therefore provided with water intakes for seawater.

However, there have arisen problems associated with damage caused by waste that clogs this water intake to restrict or stop the taking of water so that the operation of the facility is hindered.

One example of the waste includes jellyfish. Heretofore, the seaside plant facilities have taken the following countermeasures against the damage caused by the jellyfish: firstly, for the purpose of preventing the jellyfish from entering the water intakes, the jellyfish is forcedly moved using air bubbling, water-stream propellers, ships, etc., while protective nets are disposed at the water intakes; and secondly, the jellyfish is landed using rotary dust collectors, pumps, etc. and disposed of.

In the case of the first countermeasure, jellyfish may enter the water intake through gaps in the protective net. This approach also has a risk of incurring a plague of jellyfish, because the jellyfish is released alive. In addition, the cleaning or wiring procedure of the protective net is necessary due to the undesirable attachment of fouling organisms such as *Mytilus galloprovincialis* to the protective net. During this procedure, the protective net is unavailable. Furthermore, much effort must be expended on cleaning or drying the protective net. Also, enough space for this procedure must be secured. Hence, the operation and maintenance of the protective net disadvantageously requires a great deal of cost.

In the case of the second countermeasure, landed jellyfish must be disposed of. This disposal disadvantageously requires a great deal of time and effort, cost, and the like. Specifically, the jellyfish may be dried in the sun for dehydration or reduction in its volume and then disposed of. In such a case, the amount of the jellyfish disposed of largely depends on climate. In addition, the jellyfish must be dried in the sun for a period as long as several days, and a huge place is necessary for the sun-drying of large amounts of landed jellyfish at once. Also, this approach disadvantageously has a great impact, such as the generation of foul odor, on surrounding environments. Alternatively, the jellyfish may be incinerated before being disposed of. In such a case, unfortunately, it is very difficult to incinerate the jellyfish itself, because the jellyfish individual is composed of approximately 95% by mass to 98% by mass of water. Alternatively, the jellyfish may be decomposed physicochemically using pressure or chemicals (see Japanese Patent Application Laid-Open (JP-A) Nos. 2001-300505, 2000-5738, 11-244833, 2003-145196 and 2001-198566). This approach, however, requires a great deal of thermal energy or electric energy for the decomposition treatment and also disadvantageously requires a great deal of cost of, for example, installing, constructing, and maintaining treatment apparatuses. The chemical decomposition treatment of the jellyfish with an acid or an alkali disadvantageously requires neutralization after the decomposition treatment.

Also, a method for biologically decomposing the jellyfish using microorganisms or the like is known. Examples thereof include a method which involves using jellyfish-decomposing enzymes secreted by microorganisms to decompose collagen fibers, which are proteins constituting the body of the jellyfish, so that water is removed from the body of the jellyfish to reduce its volume (see JP-A Nos. 2003-53303, 11-179327, 2001-95564 and 2002-136952).

In this case, however, the decomposition of the jellyfish requires approximately 1 day and thus, cannot achieve a rapid decomposition treatment. In addition, this decomposition treatment unfavorably results in incomplete decomposition.

A plaque of jellyfish, for example, floating in seawater, often occurs mainly in warmer months and also causes various damages on locations other than the seaside plant facilities. For example, *Nemopilema nomurai Kishinouye*, which emerges in massive amounts in waters close to Japan, moves with the sea current to the coasts of various regions. This jellyfish has thus inflicted enormous damage on the coastal fishing industry such as set net fishery in recent years.

For example, jellyfish having a toxin, such as *Nemopilema nomurai Kishinouye* or *Carybdea rastoni Haacke* (also called Portuguese man-of-war), may be caught in a fishing net simultaneously with fish harvesting. The toxin of the caught jellyfish causes bleaching of fish, resulting in undesirable reduction in the commercial value of the fish.

The toxin of this jellyfish is very strong, and there have been reports of death caused by anaphylactic shock. In this regard, a further problem of the method for biologically decomposing the jellyfish is a risk of rendering the toxin accessible during the disposal of treated liquids.

Nevertheless, a method for securing the safety of such a waste liquid has not yet been known.

Thus, effective countermeasures remain to be taken against the damage caused by the jellyfish on the seaside plant facilities. Under the circumstances, there is a demand for developing related technology that can decompose the jellyfish rapidly and easily with the minimum consumption of physicochemical energy such as pressure, chemicals, or high temperature, and permits safe disposal of treated products after the decomposition.

SUMMARY OF THE INVENTION

The present invention is intended to solve the problems of the conventional techniques and attain the following object. Specifically, an object of the present invention is to provide a microorganism belonging to the genus *Bacillus*, which can produce a thrombolytic enzyme having excellent decomposing activity against waste, and a method for treating waste, which can treat the waste conveniently, rapidly, and completely without requiring a huge place and can inexpensively reduce the volume of the waste by the treatment without requiring a great deal of thermal energy or electric energy, while the method can prevent the generation of foul odor during the treatment and further offers the treated waste with high safety.

The present inventors have conducted diligent studies to attain the object and consequently fond that a method for treating waste, including a decomposition step of decomposing waste using a thrombolytic enzyme can treat the waste conveniently, rapidly, and completely without requiring a huge place and can inexpensively reduce the volume of the waste by the treatment without requiring a great deal of thermal energy or electric energy, while the method can prevent the generation of foul odor during the treatment and further offers the treated waste with high safety. On the basis of these findings, the present invention has been completed.

The present invention is based on the findings obtained by the present inventors.

The present invention provides a microorganism belonging to the genus Bacillus, wherein the microorganism belonging to the genus Bacillus is any one of a Bacillus subtilis 104-1-3-1 strain (Accession No: NITE BP-680) and a derivative strain thereof, and wherein the microorganism belonging to the genus Bacillus produces a thrombolytic enzyme which decomposes waste.

The present invention provides a thrombolytic enzyme, wherein the thrombolytic enzyme is produced by a microorganism belonging to the genus Bacillus wherein the microorganism belonging to the genus Bacillus is any one of a Bacillus subtilis 104-1-3-1 strain (Accession No: NITE BP-680) and a derivative strain thereof.

In one aspect the thrombolytic enzyme has an optimum pH of 6 to 12.

In another aspect the thrombolytic enzyme according has an optimum temperature of 20° C. to 70° C.

In yet another aspect, the thrombolytic enzyme is nattokinase.

The present invention provides a method for treating waste, including: decomposing waste with the thrombolytic enzyme wherein the thrombolytic enzyme is produced by the microorganism belonging to the genus Bacillus wherein the microorganism belonging to the genus Bacillus is any one of a Bacillus subtilis 104-1-3-1 strain (Accession No: NITE BP-680) and a derivative strain thereof.

In one aspect the thrombolytic enzyme is a thrombolytic enzyme obtained by: mixing the microorganism belonging to the genus Bacillus, wherein the microorganism belonging to the genus Bacillus is any one of a Bacillus subtilis 104-1-3-1 strain (Accession No: NITE BP-680) and a derivative strain thereof, with a proteinaceous raw material; fermenting the proteinaceous raw material with the microorganism belonging to the genus Bacillus; and separating the thrombolytic enzyme from a fermentation product obtained in the fermenting.

In one aspect the present invention provides a method for treating waste wherein the decomposing is performed in a mixture of the microorganism belonging to the genus Bacillus wherein the microorganism belonging to the genus Bacillus is any one of a Bacillus subtilis 104-1-3-1 strain (Accession No: NITE BP-680) and a derivative strain thereof, and the waste.

In one aspect the present invention provides a method for treating waste wherein the waste is jellyfish, fish, plankton, a toxin, or any combination thereof.

The present invention can solve the problems of the conventional techniques and attain the object. Specifically, the present invention can provide a microorganism belonging to the genus Bacillus, which can produce a thrombolytic enzyme having excellent decomposing activity against waste, and a method for treating waste, which can treat the waste conveniently, rapidly, and completely without requiring a huge place and can inexpensively reduce the volume of the waste by the treatment without requiring a great deal of thermal energy or electric energy, while the method can prevent the generation of foul odor during the treatment and further offers the treated waste with high safety.

BRIEF DESCRIPTION OF THE DRAWINGS

FIG. 18 is a diagram showing the relationship between a *Carybdea rastoni Haacke* toxin solution (CrTXs) and the rate of hemolysis of sheep erythrocytes in Test Example 16. The ordinate denotes the rate of hemolysis (%).

FIG. 19 is a diagram showing the thermal stability of the *Carybdea rastoni Haacke* toxin in Test Example 16. The ordinate denotes the rate of hemolysis (%).

DETAILED DESCRIPTION OF THE INVENTION

Microorganism Belonging to Genus *Bacillus*

Figure 1:
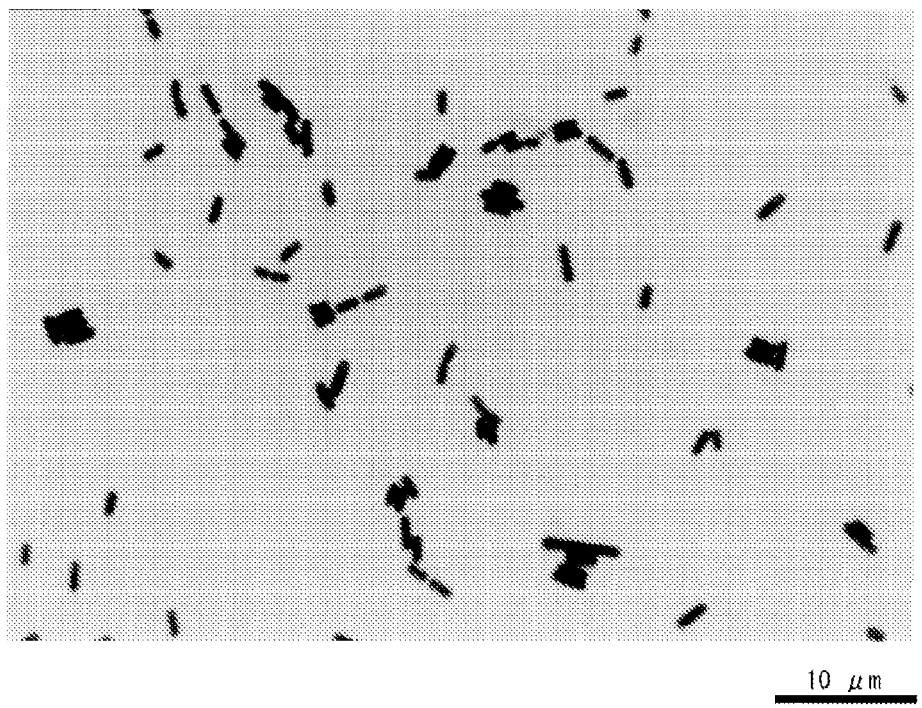
FIG. 1 is an optical micrograph of the 104-1-3-1 strain.

The microorganism belonging to the genus *Bacillus* of the present invention is any of a *Bacillus subtilis* 104-1-3-1 strain and a derivative strain thereof. This microorganism produces a thrombolytic enzyme decomposing waste.

Scientific Property

The 104-1-3-1 strain is a gram-positive *bacillus* that exhibits a chain of cells and forms spores. The swelling of the bacterial spores is not observed. This strain is in a colony form that has a diameter of 2.0 mm to 3.0 mm, a color tone of cream color, a round shape, a lens-like elevation, a wavy margin, a rough surface shape, an opaque phenotype, and a butyrous texture and is found positive for catalase reaction and negative for oxidase reaction. This strain oxidizes L-arabinose, ribose, and glucose, etc., and does not oxidize erythritol, D-arabinose, and L-xylose, etc., in the API test. The strain does not grow under anaerobic conditions and grows in a medium containing 50% by mass or 10% by mass of sodium chloride. The strain hydrolyzes casein, but does not hydrolyze starch. As a result of search based on the nucleotide sequence of the 16S rRNA gene, the 104-1-3-1 strain was considered homologous to *Bacillus subtilis* and, however, differed in some physiological properties from general *Bacillus subtilis*. From these results, the 104-1-3-1 strain was presumed to be a novel strain of *Bacillus subtilis*.

Taxonomic Position
  Bacillus sp.
Culture Condition
(1) Medium name: Nutrient agar
(2) Composition of medium: 0.5% by mass of peptone, 0.3% by mass of beef extracts, and 1.5% by mass of agar
(3) Medium pH: 7.0
(4) Condition for sterilization of medium: 121° C., 20 minutes
(5) Culture temperature: 30° C.
(6) Culture period: 7 days
(7) Oxygen requirement: aerobic
Storage Condition
(1) Freezing condition: L-drying
(2) Protectant: 20% by volume of glycerol
(3) Recovery rate after freezing: 100%
Deposition The 104-1-3-1 strain was deposited under Accession No: NITE BP-680 with National Institute of Technology and Evaluation on Nov. 21, 2008.

Derivative Strain

The derivative strain of the 104-1-3-1 strain is not particularly limited as long as this derivative strain can produce a thrombolytic enzyme decomposing waste. The derivative strain can be selected appropriately according to the purpose. Examples thereof include microorganisms belonging to the genus *Bacillus*, which have properties of the 104-1-3-1 strain altered by mutation (spontaneous or induced), transformation, conjugation, gene recombination, ultraviolet rays, radiation, chemicals, or the like.

Confirmation of Thrombolytic Enzyme Activity

The method for confirming whether or not the microorganism belonging to the genus *Bacillus* has thrombolytic enzyme activity is not particularly limited and can be selected appropriately according to the purpose. Examples thereof include the following dilution method:

The dilution method is not particularly limited and can be selected appropriately according to the purpose. Examples thereof include a method which involves diluting the microorganism belonging to the genus *Bacillus* to an appropriate concentration by suspension in distilled water, a medium, or the like, then inoculating the resulting liquid containing the microorganism belonging to the genus *Bacillus* to an agar medium containing a protein component such as fibrin, and confirming a clear digestion circle resulting from the decomposition of the protein component by a thrombolytic enzyme produced by the microorganism belonging to the genus *Bacillus*. This method can determine the presence or absence of the ability of the microorganism belonging to the genus *Bacillus* to produce a thrombolytic enzyme and can further evaluate the amount of the thrombolytic enzyme produced and its enzyme activity by the measurement of the area of the digestion circle.

The protein component in the agar medium is not particularly limited and can be selected appropriately according to the purpose from among protein components known in the art. Examples thereof include casein, hemoglobin, and fibrin. These protein components may be used alone or in combination of two or more thereof.

Culture

The microorganism belonging to the genus *Bacillus* can grow in a medium known in the art even under culture conditions other than those described above. This growth may be achieved by liquid culture or solid culture.

The composition of the medium is not particularly limited as long as this medium permits propagation of the microorganism belonging to the genus *Bacillus* so as to produce the thrombolytic enzyme. The medium can be selected appropriately according to the purpose. Examples thereof include media containing medium components known in the art, such as carbon sources, nitrogen sources, and inorganic salts. These medium components may be used alone or in combination of two or more thereof.

The nitrogen sources are not particularly limited and can be selected appropriately according to the purpose. Examples thereof include commercially available soybean flour, peptone, yeast extracts, meat extracts, corn steep liquor, and ammonium sulfate.

The carbon sources are not particularly limited and can be selected appropriately according to the purpose. Examples thereof include hydrocarbons and fats, such as tomato paste, glycerin, starch, glucose, galactose, and dextrin.

The inorganic salts are not particularly limited and can be selected appropriately according to the purpose. Examples thereof include common salt, and calcium carbonate.

The medium may also be supplemented, if necessary, with a trace amount of a metal salt or a component known in the art to enhance the amount of the thrombolytic enzyme produced.

These materials are not limited as long as the materials can be utilized by the microorganism belonging to the genus *Bacillus* and help the microorganism produce the thrombolytic enzyme. Any of culture materials known in the art can be used.

The culture method is not particularly limited and can be selected appropriately according to, for example, the type of the microorganism belonging to the genus *Bacillus*, from among methods known in the art. Examples thereof include various methods such as batch culture, semicontinuous culture, and continuous culture methods. Methods known in the art for promoting the growth of the microorganism belonging to the genus *Bacillus* may be used in combinations for the culture.

Conditions for culture using the liquid medium are not particularly limited as long as the microorganism belonging to the genus *Bacillus* can produce the thrombolytic enzyme without being killed under these conditions. The conditions can be selected appropriately according to the purpose.

The culture temperature is not particularly limited and can be selected appropriately according to the purpose. The culture temperature is preferably 10° C. to 45° C., more preferably 27° C. to 40° C., particularly preferably 27° C. to 30° C. This particularly preferable range is advantageous because the thrombolytic enzyme is produced in large amounts.

The culture time is not particularly limited and can be selected appropriately according to the purpose. The culture time is preferably 12 hours to 120 hours, more preferably 48 hours to 96 hours.

The culture may be aerobic culture or anaerobic culture. The aerobic culture is preferable because the microorganism belonging to the genus *Bacillus* efficiently propagates. Also, shake culture or static culture may be performed.

The method for confirming the successful propagation of the microorganism belonging to the genus *Bacillus* in the liquid medium is not particularly limited and can be selected appropriately according to the purpose. Examples thereof include: a method which involves confirming, by visual observation or absorbance measurement, change in the turbidity of a liquid medium for enrichment culture or change in color caused by an added reagent; a method which involves confirming the propagation of the microorganism by gel permeation chromatography measurement; and a method which involves confirming the propagation of the microorganism by the measurement of a chemical oxygen demand.

Use

The microorganism belonging to the genus *Bacillus* can efficiently produce a thrombolytic enzyme and as such, can be used preferably in the method for treating waste according to the present invention.

Thrombolytic Enzyme

The thrombolytic enzyme of the present invention is an enzyme that is produced by the microorganism belonging to the genus *Bacillus* of the present invention and lyses a thrombus-forming protein called fibrin.

The thrombolytic enzyme produced by the microorganism belonging to the genus *Bacillus* is not particularly limited and can be selected appropriately according to the purpose. Examples thereof include nattokinase, plasmin, and trypsin.

The nattokinase, a serine thrombolytic enzyme, belongs to the subtilisin family and was found from *Bacillus subtilis* (natto *bacillus*) that has been taken as foods such as natto since ancient times. This enzyme is known to have strong fibrinolytic activity. Natto has been eaten as traditional foods since ancient times. In addition, many natto-like traditional foods are eaten in South-East Asian countries. This means that the safety of natto has been verified over a long period of time. Enzymes belonging to the subtilisin family have been utilized so far as cleaning ingredients in detergents. The nattokinase can be used preferably without problems in the waste treatment of the present invention described later, in terms of the safety of the enzymes and because particular problems or accidents attributed to wastewater containing the enzymes have not been reported in previous cases.

The whole amino acid sequence of the nattokinase has already been determined (see JP-A Nos. 06-153977 and 2006-325538; T. Nakamura et al (1992) Biosci. Biotech. Biochem., 56, 1869-1871; and T. Urano et al (2001) J. Biol. Chem., 27, 24690-24696).

The nattokinase produced by the microorganism belonging to the genus *Bacillus* of the present invention has the amino acid sequence represented by SEQ ID NO: 3. This amino acid sequence exhibits 100% identity to the amino acid sequence of the nattokinase gene (Accession No: P35835) registered in GenBank.

The method for isolating the thrombolytic enzyme produced by the microorganism belonging to the genus *Bacillus* is not particularly limited and can be selected appropriately according to the purpose. Examples thereof include a method which involves culturing microorganism belonging to the genus *Bacillus* by liquid culture or solid culture and disrupting the obtained bacterial cells by sonication or using a drug (e.g., lysozyme) having the effect of disrupting the bacterial cells of the microorganism belonging to the genus *Bacillus*, to thereby isolate the enzyme.

The method for confirming the enzyme activity of the thrombolytic enzyme and the amount of the thrombolytic enzyme produced is not particularly limited and can be selected appropriately according to the purpose from among methods known in the art. Examples thereof include: a method which involves inoculating the culture supernatant of the microorganism belonging to the genus *Bacillus* to an agar medium or the like containing a protein component, and confirming a clear digestion circle resulting from the decomposition of the protein component by the thrombolytic enzyme produced by the microorganism belonging to the genus *Bacillus*; and a method which involves reacting a protein component with a culture supernatant with an arbitrary bacterial concentration to prepare a calibration curve.

Method for Treating Waste

The treatment method of the present invention includes at least a decomposition step of decomposing waste using the thrombolytic enzyme of the present invention and optionally includes an additional step.

Decomposition Step

The decomposition step is the step of decomposing waste using the thrombolytic enzyme.

Waste

The waste is not particularly limited as long as this waste can be decomposed by the thrombolytic enzyme. The waste can be selected appropriately according to the purpose and is preferably organic waste, more preferably waste containing an amino acid or a protein. The protein may be a resistant protein that cannot be lysed even by the action of proteinase K in an amount of 0.1% by mass under conditions of 30° C. for 120 minutes. The method for treating waste is particularly preferably applied to marine industrial waste including marine organisms or freshwater organisms. In addition, the method for treating waste is advantageous because this method can also be applied preferably to the decomposition of a toxin produced in or from such waste. Such waste may be used alone or in combination of two or more thereof.

The marine industrial waste (marine organisms and freshwater organisms) is not particularly limited and can be selected appropriately according to the purpose. Examples thereof include fishery products, plankton, sponges, hydrozoans, tube-building polychaetes, *Bryozoa*, amphipod, skeleton shrimps, ascidian, crustaceans, and flatworms.

The fishery products are not particularly limited and can be selected appropriately according to the purpose. Examples thereof include: fish such as puffers; and shellfish belonging to the families Pectimidae (e.g., scallop), Ostreidae (e.g., oyster), Spiraxidae (e.g., *Euglandina rosea*), Mytilidae (e.g., *Limnoperna fortunei, Mytilus galloprovincialis, Perna viridis*, and *Xenostrobus securis*), Dreissenidae (e.g., *Dreissena polymorpha, Dreissena bugensis*, and *Mytilopsis sallei*), Nassariidae (e.g., *Nassarius sinarus*), Corbiculidae (e.g., *Corbicula fluminea*), Veneridae (e.g., *Meretrix petechialis*), Achatimidae (e.g., *Achatina fulica*), Ampullariidae (e.g., *Pomacea canaliculata*), Conidae (e.g., cone shell), Octopodidae (e.g., blue-ringed octopus), and Nassariidae (e.g., *Nassarius glans*).

The fishery products disadvantageously become waste in aquatic food processing or attach to intake pipes or the like in power plants. Since the puffers are fish having a deadly poison, their non-edible portions are waste. These fishery products may be used alone or in combination of two or more thereof.

The plankton is not particularly limited and can be selected appropriately according to the purpose. Examples thereof include: jellyfish belonging to the families Coelenterata, Rhizostomidae (e.g., *Rhopilema esculenta* and *Nemopilema nomurai Kishinouye*), Carybdeidae, and Pelagiidae (e.g., *Chrysaora hysocella*); red tide phytoplankton such as cyanobacteria, blue-green algae, and *Anabaena* sp.; and microalgae including benthic diatoms such as green algae, diatoms, dinoflagellates, and *Dictyocha fibula*. These organisms may be used alone or in combination of two or more thereof.

The thrombolytic enzyme can preferably decompose collagen constituting the body components of jellyfish.

The crustaceans are not particularly limited and can be selected appropriately according to the purpose. Examples thereof include crustaceans belonging to the families Grapsidae (e.g., *Eriocheir japonica*), Astacidae (e.g., *Astacus* sp. and *Pacifastacus leniusculus trowbridgii* (signal crayfish)), Cambaridae (e.g., *Procambarus clarkii* and *Orconectes rusticus*), Parastacidae (e.g., *Cherax* sp.), Portunidae (e.g., *Carcinus aestuarii* and *Carcinus maenas*), Balanidae (e.g., barnacles and *Balanus amphitrite*), and Xanthidae (e.g., *Atergatis floridus*).

The flatworms are not particularly limited and can be selected appropriately according to the purpose. Examples thereof include flatworms belonging to the family Rhynchodemidae (e.g., *Platydemus manokwari*).

The toxin is not particularly limited and can be selected appropriately according to the purpose. Examples thereof include a jellyfish toxin and a puffer toxin.

The jellyfish toxin is not particularly limited and can be selected appropriately according to the type of jellyfish. Examples thereof include the *Carybdea rastoni Haacke* toxin CrTXs, the *Chironex yamaguchii* toxin CqTX-A, and the *Carybdea alata* toxin CaTX-A. These toxins may be used alone or in combination of two or more thereof.

The Invasive Alien Species Act (Law No. 78 of Jun. 2, 2004 in Japan) designate organisms causing harm to ecosystems, human safety, or the agriculture, forestry and fisheries industry as invasive alien species. The law regulates the feeding, cultivation, storage, transport, import, and the like of the invasive alien species and requires the national and local governments to remove alien species in the field, etc., according to the need. The method for treating waste according to the present invention can also be used preferably for the invasive alien species.

Examples of the invasive alien species include: shellfish such as *Euglandina rosea, Limnoperna* sp., *Dreissena polymorpha*, and *Dreissena bugensis*; crustaceans such as *Eriocheir* sp. (except for *Eriocheir japonica*), *Astacus* sp., *Pacifastacus leniusculus trowbridgii* (signal crayfish), *Orconectes rusticus*, and *Cherax* sp.; and flatworms such as *Platydemus manokwari*.

Examples of precautious alien species include: shellfish such as *Mytilus galloprovincialis, Perna viridis, Nassarius sinarus, Xenostrobus securis, Mytilopsis sallei, Corbicula fluminea, Meretrix petechialis, Achatina fulica*, and *Pomacea canaliculata*; and crustaceans such as *Procambarus clarkii, Carcinus aestuarii, Carcinus maenas*, and *Balanus amphitrite*.

The method for treating waste can also be applied to the treatment of the alien species as well as toxic species including: toxic shellfish such as cone shell, blue-ringed octopus, and *Nassarius glans*; and toxic crustaceans such as *Atergatis floridus*, particularly, to treatment such as termination of a plague of the toxic species.

The waste may be used directly after collection or may be subjected to appropriate pretreatment such as heat treatment or physical disruption.

In the case where the waste is jellyfish, the whole individuals may be used directly. Preferably, the jellyfish, depending on its type, is appropriately physically disrupted in terms of a short treatment time and improved treatment efficiency. When the jellyfish is physically disrupted, its size is not particularly limited and can be selected appropriately according to the purpose. The jelly fish is disrupted into preferably 20 cm or less square, more preferably 10 cm or less square, particularly preferably 3 cm or less square.

The waste may be frozen after collection and melted for use, for example, or may be used in a water-removed state or in a water-containing state.

The water is not particularly limited and can be selected appropriately according to the purpose. Examples thereof include purified water, tap water, and seawater.

The method for treating waste can directly treat the waste even in seawater, which contains salt, and is thus advantageous because the method can achieve convenient treatment without requiring a huge place.

Thrombolytic Enzyme

In the decomposition step, the thrombolytic enzyme may be used in combination with an additional enzyme.

The additional enzyme is not particularly limited and can be selected appropriately according to the purpose.

The enzyme for use in the decomposition step of the present invention is a thrombolytic enzyme produced by the 104-1-3-1 strain and may be used in combination with a thrombolytic enzyme known in the art.

The state of the thrombolytic enzyme is not particularly limited and can be selected appropriately according to the purpose. Examples thereof include a culture liquid containing the microorganism belonging to the genus *Bacillus*, a culture supernatant after removal of the bacterial cells of the microorganism belonging to the genus *Bacillus*, and those treated in an additional step described later.

The thrombolytic enzyme-producing microorganism belonging to the genus *Bacillus* may be used in the decomposition step in a state immobilized on a carrier.

The carrier is not particularly limited, and its shape, structure, size, material, and the like can be selected appropriately according to the purpose, etc.

Examples of the shape of the carrier include spherical, granular, massive (pellet), sheeted, columnar, net-like, and capsule shapes. These shapes may be used alone or in combination of two or more thereof.

The structure of the carrier may be constituted of one member alone or may be constituted of two or more members. The carrier may have a single-layer structure or a multilayer structure. These structures may be used alone or in combination of two or more thereof.

The microstructure of the carrier is not particularly limited as long as, for example, this structure allows the microorganism belonging to the genus *Bacillus* to come into contact with the waste. For example, a porous or net-like structure is preferable. The carrier having this structure can increase the area of the contact between the microorganism belonging to the genus *Bacillus* immobilized on the carrier and the waste and is thus advantageous in terms of the excellent decomposition efficiency of the waste.

The size of the carrier can be selected appropriately according to the size, etc. of a container or the like housing the carrier. A plurality of the carriers may have equal (constant) sizes or may differ in size from each other.

Preferable examples of the material of the carrier include polysaccharides, proteins, synthetic polymers, and inorganic substances. These materials may be used alone or in combination of two or more thereof.

Examples of the polysaccharides include cellulose, dextran, agarose, sodium alginate, agar, and carrageenan. Among them, agar is preferable because the agar can retain the microorganism belonging to the genus *Bacillus* at a high concentration while it is excellently permeable to components in waste liquid and is easily granulated and easily treated or disposed of, with little toxicity.

The proteins are preferably, for example, inactivated proteins. Examples thereof particularly include gelatin, albumin, and collagen.

Examples of the synthetic polymers include acrylamide, polyvinyl alcohol, polyethylene glycol, sodium polyacrylate, polyvinyl chloride, polystyrene, polyurethane, and photocurable resins.

Examples of the inorganic substances include silica gel, activated carbon, sand, porous glass, anthracite, zeolite, expanded-clay, and liquid slag. Among them, the porous material silica gel or activated carbon is preferable.

The method for immobilizing the microorganism belonging to the genus *Bacillus* onto the carrier is not particularly limited. The method can be performed according to a method known in the art and can be selected appropriately according to the purpose. Preferable examples thereof include a deposition method (carrier binding method), a cross-linking method, and an entrapment method. These methods may be adopted alone or may be used in combination of two or more thereof.

The deposition method (carrier binding method) involves immobilizing the microorganism belonging to the genus *Bacillus* onto the surface of the carrier insoluble in water. The cross-linking method involves cross-linking the microorganism belonging to the genus *Bacillus* to a reagent having two or more functional groups. The entrapment method involves entrapping the microorganism belonging to the genus *Bacillus* in the lattice of a gel (lattice type) or coating the microorganism with a polymer film (microcapsule).

When the microorganism belonging to the genus *Bacillus* is immobilized onto the carrier, the position at the microorganism belonging to the genus *Bacillus* is immobilized is not particularly limited and can be selected appropriately according to the purpose, etc. Since the microorganism belonging to the genus *Bacillus* is aerobic, the microorganism is preferably immobilized on or near the surface of the carrier.

The production of a carrier gel as the carrier for immobilization using agar will be described below.

For the carrier, the agar is preferably granulated at a concentration of, for example, 3% by mass that reduces the leakage of the immobilized microorganism belonging to the genus *Bacillus* or the invasion thereof into the inside of the carrier and renders the carrier excellently durable, long-life, and highly stable.

The agar is mixed with water to adjust the agar concentration to 3% by mass. The agar is dissolved therein with stirring at 60° C. or higher. For the stable immobilization of the heat-labile microorganisms belonging to the genus *Bacillus*, the resulting agar is preferably mixed with the microorganisms belonging to the genus *Bacillus* at the lowest possible temperature (e.g., 55° C. or lower) without being solidified.

The microorganisms belonging to the genus *Bacillus* used can be collected, for example, by operation such as centrifugation.

The agar mixed with the microorganisms belonging to the genus *Bacillus* is solidified by cooling to room temperature, then placed in a molding container, and cut into the desired shape to thereby obtain a carrier with the immobilized microorganisms belonging to the genus *Bacillus*.

The carrier with the immobilized microorganisms belonging to the genus *Bacillus* (hereinafter, also referred to as a "*Bacillus* microorganism-immobilized carrier") is preferably housed in a container for contact with the waste. The carrier thus housed in the container is preferable because the carrier can be contacted with the waste efficiently and in a controlled manner.

The container is not particularly limited, and its shape, structure, size, material, and the like can be selected appropriately according to the purpose.

Preferable examples of the shape of the container include a cylindrical shape.

The material of the container is preferably a salt-tolerant material. More preferably, the container is made of glass, a resin, stainless, or the like. Among them, a material that renders the inside of the container visible is preferable.

The filling rate of the *Bacillus* microorganism-immobilized carrier in the container is not particularly limited and can be selected appropriately according to the purpose. The filling rate may be 100% or may be less than 100%.

A plurality of the containers may be connected in parallel or in series according to the load of waste.

Decomposition Method

The waste can be decomposed by its contact with the thrombolytic enzyme.

When the culture liquid containing the microorganism belonging to the genus *Bacillus* is directly used as the thrombolytic enzyme, the decomposition step may involve causing the microorganism belonging to the genus *Bacillus* to produce the thrombolytic enzyme in a liquid mixture of the microorganism belonging to the genus *Bacillus*, the waste, and preferably a medium suitable for culture of the microorganism belonging to the genus *Bacillus*, while decomposing the waste. This method is preferable in terms of convenient operation and the treatment of the waste achieved in a short time.

Also, the decomposition step may be performed using an apparatus. The apparatus is not particularly limited and can be selected appropriately according to the purpose. Examples thereof include a wet treatment apparatus described in JP-A No. 2005-262105.

The amount of the waste used in the decomposition step is not particularly limited and can be selected appropriately according to the purity of the thrombolytic enzyme, the titer of the thrombolytic enzyme, etc.

The amount of the thrombolytic enzyme used in the decomposition step is not particularly limited and can be selected appropriately according to the purity of the thrombolytic enzyme, the titer of the enzyme, etc. The amount is preferably 0.1% by volume or more, more preferably 1% by volume or more, further preferably 1% by volume to 2% by volume, with respect to the volume of the waste. The thrombolytic enzyme used in an amount less than 0.1% by volume may require a longer time for the waste treatment or may reduce decomposition efficiency. The thrombolytic enzyme used in an amount exceeding 2% by volume may no longer enhance treatment efficiency and is thus disadvantageous in terms of cost. The upper limit, however, is not critically significant for the decomposition treatment.

Preferably, the thrombolytic enzyme is further added in an amount required for the decomposition of the waste, if necessary, during the decomposition treatment to thereby keep its concentration constant in the treating liquid.

The amount of water in the treating liquid during the decomposition treatment is not particularly limited and can be selected appropriately according to the purpose. The amount is preferably 25% by volume or more, more preferably 50% by volume to 70% by volume. The water in an amount less than 25% by volume may impede the enzyme-mediated decomposition reaction due to the insufficient contact between waste and the enzyme. The water in an amount exceeding 70% by volume may dilute the enzyme to thereby slow down the decomposition reaction rate.

The temperature of the decomposition treatment is not particularly limited as long as the waste can be decomposed at this temperature. The temperature can be selected appropriately according to the type of the thrombolytic enzyme, the amount of the waste, etc., and is preferably 20° C. to 70° C., more preferably 30° C. to 60° C., particularly preferably 40° C. to 53° C. A decomposition temperature lower than 20° C. may require a longer time for the treatment or may reduce decomposition efficiency. A decomposition temperature exceeding 70° C. may inactivate the thrombolytic enzyme, resulting in unsuccessful decomposition of the waste.

When the waste is easily decomposable and can be decomposed through reaction in a short time, the temperature is preferably 45° C. to 70° C., more preferably 50° C. to 60° C., in terms of the high initial enzyme activity of the thrombolytic enzyme.

When the waste is poorly decomposable and requires long-time reaction for its decomposition, the temperature is preferably 30° C. to 50° C., more preferably 40° C. to 47° C., in terms of the stability of the thrombolytic enzyme.

The pH of the decomposition treatment is not particularly limited and can be selected appropriately according to the type of the thrombolytic enzyme, etc. The pH is preferably 6 to 12, more preferably 6 to 9. A pH less than 6 or exceeding 12 may inactivate the thrombolytic enzyme, resulting in insufficient decomposition of the waste.

The time of the decomposition treatment is not particularly limited and can be selected appropriately according to the type or amount of the thrombolytic enzyme, the type or amount of the waste, etc. The time is preferably 5 minutes or longer, more preferably 10 minutes or longer. The upper limit of the reaction time is not particularly limited and can be selected appropriately according to the purpose. The time is preferably 2 hours or shorter. In most cases, the waste, depending on its type, is completely decomposed within 2 hours. Thus, reaction for a time exceeding 2 hours may be inefficient.

In the decomposition step, the waste, depending on its type, becomes liquid and is thus advantageous in terms of its removal easily achieved.

Additional Step

The additional step is not particularly limited and can be selected appropriately according to the purpose. Examples thereof include a purification step, a fermentation product preparation step, and a drying step.

Purification Step

The purification step is the step of purifying the thrombolytic enzyme.

The method for purifying the thrombolytic enzyme is not particularly limited and can be selected appropriately according to the purpose. Examples thereof include a method which involves fractionating, for example, the thrombolytic enzyme-containing culture supernatant of the microorganism belonging to the genus *Bacillus*, by hydrophobic interaction chromatography, then desalting the desired fractions by gel filtration chromatography, and purifying the desalted fractions by density gradient isoelectric focusing.

Fermentation Product Preparation Step

The fermentation product preparation step is the step of mixing the thrombolytic enzyme-producing microorganism belonging to the genus *Bacillus* with a proteinaceous raw material, and fermenting the proteinaceous raw material therewith to obtain a fermentation product. The serum-lytic enzyme for use in the decomposition step may be separated from the fermentation product.

The method for preparing the fermentation product is not particularly limited and can be selected appropriately according to the purpose. Examples thereof include a method which involves mixing a proteinaceous raw material with the microorganism belonging to the genus *Bacillus* and fermenting the proteinaceous raw material by a method known in the art.

The proteinaceous raw material is not particularly limited and can be selected appropriately according to the purpose. Examples thereof include: plant-derived raw materials such as soybeans, red beans, kidney beans, peas, fava beans, mottled kidney beans, red kidney beans, and peanuts; and animal-derived raw materials such as butcher meat, fish meat, and chicken meat. These materials may be used alone or in combination of two or more thereof.

The fermentation temperature is not particularly limited and can be selected appropriately according to the purpose. The fermentation temperature is preferably 10° C. to 50° C., more preferably 27° C. to 40° C.

The fermentation time is not particularly limited and can be selected appropriately according to the purpose. The fermentation time is preferably 20 hours to 72 hours, more preferably 48 hours to 72 hours.

The method for separating the fermentation product is not particularly limited and can be selected appropriately according to the purpose. Examples thereof include a method which involves separating the fermentation product by salting out or various chromatography techniques.

Drying Step

The drying step is the step of drying the thrombolytic enzyme. This step is preferable because the resulting thrombolytic enzyme for use in the decomposition step can be stored for a long period and is easily and appropriately available in a suitable amount for use.

The drying method is not particularly limited and can be performed by an approach known in the art. A usual method can be used, for example, freeze-drying, circulation drying, drying by heating, or drying under reduced pressure.

Alternatively, the thrombolytic enzyme may be remelted in a solvent suitable for the purpose after freeze-drying. The thrombolytic enzyme has stable enzymatic activity even after freeze-drying and is thus advantageous in terms of high storage stability.

In this context, examples of the dried thrombolytic enzyme include dried products of a culture liquid containing the microorganism belonging to the genus *Bacillus*, the culture supernatant of the microorganism belonging to the genus *Bacillus*, the thrombolytic enzyme purified by the purification step, and the fermentation product separated by the fermentation product preparation step.

Hereinafter, an aspect using an apparatus will be described as one aspect of the method for treating waste according to the present invention with reference to the drawing. However, the method for treating waste according to the present invention is not limited to this aspect. In the description below, the method for treating jellyfish as the waste will be described as an example. However, the waste used in the method using the apparatus may be any waste and is not limited to the jellyfish.

Figure 22:
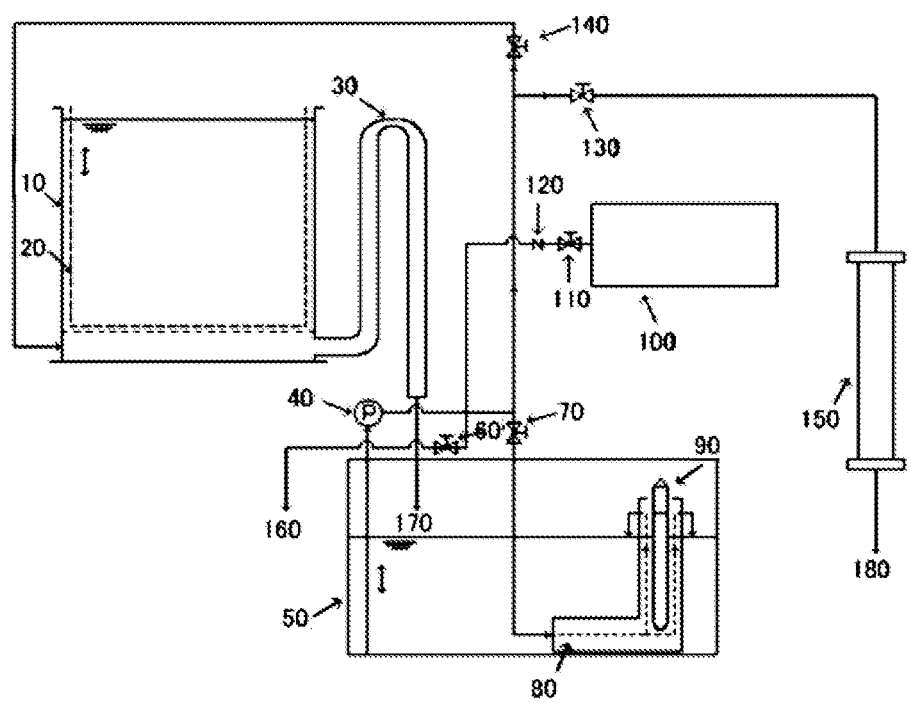
FIG. 22 is a schematic diagram illustrating one example of an apparatus used in the method for treating waste according to the present invention.

FIG. 22 is a schematic diagram illustrating one example of an apparatus (wet treatment apparatus) for use in the method for treating waste. The apparatus is based on a siphon system. The features of this apparatus are that, for example, (1) it does not require a stirring apparatus in a decomposition tank, (2) since it is operable with one pump, running cost can be reduced and maintenance management can be simplified, (3) a lysate does not flood from the decomposition tank, (4) the manner of decomposition can be observed easily, (5) the size of the apparatus can be increased easily, and (6) continuous decomposition can be achieved.

In the apparatus shown in FIG. 22, a treating liquid containing a thrombolytic enzyme produced by the microorganism belonging to the genus *Bacillus* (hereinafter, this treating liquid is also referred to as a "composition for jellyfish decomposition") is contained in advance in a circulation/ heating tank 50. A gate valve 140 in the piping is "opened", while a gate valve 60, a gate valve 70, a gate valve 110, and a gate valve 130 are "closed". In this state, a liquid feed pump 40 disposed in the piping is driven to pump the composition for jellyfish decomposition and transport it into a decomposition tank 10. The resulting composition for jellyfish decomposition is flowed into the decomposition tank 10 from the liquid inlet to come into contact with jellyfish contained in a partitioning tank 20 so that the jellyfish is contact-treated by the composition for jellyfish decomposition. In this treatment, the jellyfish is contact-treated so as to be pushed up by the composition for jellyfish decomposition flowed into the decomposition tank 10 from below. In other words, the jellyfish drops in the direction of gravitational force, whereas the composition for jellyfish decomposition comes in contact with this dropping jellyfish to push up the jellyfish. Therefore, the contact treatment is effectively performed by the synergistic effects of the gravity applied to the jellyfish and the fluid pressure of the composition for jellyfish decomposition to thereby efficiently decompose the jellyfish. Note that, in FIG. 22, reference numeral 100 denotes an ozone generator, 120 denotes a check valve, 150 denotes an activated carbon treatment tube, 160 denotes jellyfish lysate, and 180 denotes clean wastewater passed through the activated carbon treatment tube.

A portion of the composition for jellyfish decomposition flowed into the decomposition tank 10 is discharged into a siphon tube 30 from the liquid outlet disposed at the bottom of the decomposition tank 10. Then, with increase in the fluid volume (rise in water level) of the composition for jellyfish decomposition flowed into the decomposition tank 10, the fluid volume of the composition for jellyfish decomposition is also increased (water level is raised) at a similar rate in the siphon tube 30, which is connected to the liquid outlet of the decomposition tank 10 so as to extend upward from near the liquid outlet and be curved downward in the neighborhood of the upper region of the decomposition tank 10. When the fluid volume (water level) of the composition for jellyfish decomposition in the siphon tube 30 reaches the curved portion of the siphon tube 30, the composition for jellyfish decomposition in the decomposition tank 10 is continuously transported to the outside through the siphon tube 30 from the liquid outlet by the principles of siphon and continuously transported into the circulation/heating tank 50 from an end 170 of the siphon tube 30 (reference numeral 170 denotes an outlet for treated liquid passed through the siphon tube). In the partitioning tank 20, the jellyfish drops by the self-weight along with decrease in the amount of the composition for jellyfish decomposition. When the composition for jellyfish decomposition is completely transported to the outside, the jellyfish collides with the bottom surface of the partitioning tank 20 and is broken into pieces due to this collision or the like.

The composition for jellyfish decomposition transported into the circulation/heating tank 50 is lifted again by the driven liquid feed pump 40 disposed in the piping and transported again into the decomposition tank 10. As a result, the second contact treatment is performed in the decomposition tank 10. In this treatment, the gate valve 140 in the piping is "opened", while the gate valve 60, the gate valve 70, the gate valve 110, and the gate valve 130 are "closed". The liquid feed pump 40 disposed in the piping can be continuously driven to thereby continuously repeat the re-transportation into the decomposition tank 10 and the re-contact treatment in decomposition tank 10. A plurality of runs of this contact treatment completely decompose the jellyfish contained in the partitioning tank 20 so that the jellyfish is lysed into the composition for jellyfish decomposition.

In the circulation/heating tank 50, the composition for jellyfish decomposition transported through the siphon tube 30 can be passed, if necessary, through a heating tube 80 and circulated to thereby achieve heating or reaction. In other words, the composition for jellyfish decomposition is uniformly mixed by passing through the heating tube 80 and circulation in the circulation/heating tank 50. In addition, the composition for jellyfish decomposition is heated by a heater 90 to the optimum temperature for the thrombolytic enzyme contained therein (this operation of the heater 90 is not necessary if the temperature of the composition for jellyfish decomposition has already reached the optimum temperature for the enzyme contained therein) to thereby completely and efficiently decompose undecomposed jellyfish debris, etc. (jellyfish protein) contained in the composition for jellyfish decomposition. The resulting composition for jellyfish decomposition is prepared as a solution containing a uniform lysate of the jellyfish protein. In order to pass the composition for jellyfish decomposition in the circulation/heating tank 50 through the heating tube 80 and circulate it in the circulation/heating tank 50, the liquid feed pump 40 disposed in the piping can be driven in a state where the gate valve 70 in the piping is "opened", while the gate valve 60, the gate valve 130, and the gate valve 140 are "closed". In this case, the whole composition for jellyfish decomposition in the circulation/heating tank 50 may be passed through the heating tube 80 and circulated in the circulation/heating tank 50. Alternatively, a portion of the composition for jellyfish decomposition in the circulation/heating tank 50 may be passed through the heating tube 80 and circulated in the circulation/heating tank 50, while the remaining portion may be transported into the decomposition tank 10.

Use

The method for treating waste can treat the waste conveniently, rapidly, and completely without requiring a huge place and can inexpensively reduce the volume of the waste by the treatment without requiring a great deal of thermal energy or electric energy, while the method can prevent the generation of foul odor during the treatment and further offers the treated waste with high safety. Accordingly, the method for treating waste can be used preferably in the treatment of waste containing various proteins and can be used particularly preferably in seaside industrial facilities such as power plants, the treatment of bycatch marine waste in the fishing industry or the like, and the treatment of marine industrial waste such as freshwater organism waste.

The waste with the volume reduced by the thrombolytic enzyme is treated, for example, by a treatment method known in the art such as wastewater treating, into a level that permits discharge into ocean, river, or the like.

EXAMPLES

Hereinafter, the present invention will be described specifically with reference to Examples of the present invention. However, the present invention is not limited to these Examples by any means.

Test Example 1

Screening for Microorganism Having Ability to Produce Protease

Soil samples were collected from the bottom mud of the sea area off the coast of Miura-shi, Kanagawa, Japan. Dilution series were prepared from microorganisms in the soil samples and screened for a microorganism having the ability to produce protease. The bottom mud (sludge) of the sea was collected using Bacteria Core Sampler (manufactured by Rigo Co., Ltd.).

1 g each of the collected soil samples was added to 9 mL of sterile physiological saline, suspended therein, and then left at room temperature for approximately 1 hour. Next, a supernatant was separated from each thus-prepared soil suspension in physiological saline containing solid precipitates, and 9 mL of the sterile physiological saline was newly added thereto. This procedure was repeated to prepare dilution series.

100 µL each of the prepared dilution series was used and spread over a protein-containing agar medium shown below. Microorganisms were grown by static culture at 30° C. for 3 days. When the microorganism produces protease, proteins are lysed by the protease to give a clear digestion circle around the grown microorganism. A microorganism colony containing the microorganisms thus confirmed to have the ability to produce protease was extracted.

—Composition of Protein-Containing Agar Medium (pH 8.0)—

[1.5% By Mass of Agar Solution (Lower Layer)]

| Difco Marine Agar | 5.51% by mass |
|---|---|

[0.8% By Mass of Agar and 1.5% by Mass of Skimmed Milk Solution (Upper Layer)]

| Difco Marine Agar | 0.8% by mass |
|---|---|
| Skimmed milk | 1.5% by mass |

One type of microorganism with high protease activity that was derived from the bottom mud soil of the sea in Kanagawa, Japan, and thus screened for by the enrichment culture was designated as a 104-1-3-1 strain and used in tests shown below. The optical micrograph of the 104-1-3-1 strain is shown in FIG. 1.

Test Example 2

Identification of Microorganism 16S rDNA-Full Analysis and Molecular Phylogenetic Analysis The 104-1-3-1 strain was aerobically cultured at 30° C. for 24 hours in a medium (Nutrient agar, manufactured by Oxoid Ltd., Hampshire, the UK).

DNA was extracted from the cultured 104-1-3-1 strain using a DNA extraction kit (InstaGene Matrix, manufactured by Bio-Rad Laboratories, Inc.) and amplified by PCR using Prime STAR HS DNA Polymerase (manufactured by Takara Bio Inc.). Subsequently, the PCR product was sequenced (ABI PRISM 3100 Genetic Analyzer System, manufactured by Applied Biosystems Inc.) as a template using primers 9F, 339F, 785F, 1099F, 536R, 802R, 1242R, and 1510R (BigDye Terminator v3.1 Cycle Sequencing Kit, manufactured by Applied Biosystems Inc.).

The gene sequence was analyzed using analysis software (Auto Assembler, manufactured by Applied Biosystems Inc., and DNASIS Pro, manufactured by Hitachi Software Engineering Co., Ltd.).

Also, homology search was conducted using a bacterial type strain database (TechnoSuruga Laboratory Co., Ltd.) and the International Nucleotide Sequence Database (GenBank/DDBJ/EMBL).

As a result of homology search on the bacterial type strain database using BLAST, the 16S rDNA nucleotide sequence of the 104-1-3-1 strain exhibited high homology to *Bacillus*-derived 16S rDNA, as shown in Table 1 below, and particularly exhibited the highest homology to the 16S rDNA of a *Bacillus subtilis* IAM12118 strain (99% homology).

As a result of homology search on the International Nucleotide Sequence Database, the 16S rDNA nucleotide sequence of the 104-1-3-1 strain also exhibited high homology to *Bacillus subtilis*-derived 16S rDNA, as shown in Table 2 below.

TABLE 1

| Registered name | Strain name | Accession No. | Homology |
|---|---|---|---|
| *Bacillus subtilis* | IAM 12118 | AB042061 | 1508/1510 = 99.9% |
| *Bacillus vallismortis* | DSM11031 | AB021198 | 1500/1506 = 99.6% |
| *Bacillus mojavensis* | IFO15718 | AB021191 | 1496/1502 = 99.6% |
| *Bacillus atrophaeus* | JCM9070 | AB021181 | 1479/1491 = 99.2% |
| *Bacillus licheniformis* | DSM 13 | X68416 | 1485/1511 = 98.3% |
| *Bacillus axarquiensis* | CR-119 | AY603657 | 1483/1505 = 98.5% |
| *Bacillus subtilis* subsp. *spizizenii* | NRRL B-23049 | AF074970 | 1406/1409 = 99.8% |
| *Bacillus malacitensis* | CR-95 | AY603656 | 1414/1420 = 99.6% |
| *Bacillus velezensis* | CR-502 | AY603658 | 1398/1404 = 99.6% |
| *Bacillus amyloliquefaciens* | ATCC 23350 | X60605 | 1406/1430 = 98.3% |
| *Bacillus sonorensis* | NRRL B-23154 | AF302118 | 1381/1410 = 97.9% |
| *Bacillus aquimaris* | TF-12 | AF483625 | 1433/1494 = 95.9% |
| *Bacillus shackletonii* | LMG 18435 | AJ250318 | 1429/1493 = 95.7% |
| *Bacillus pumilus* | ATCC 7061 | AY876289 | 1386/1432 = 96.8% |
| *Bacillus marisflavi* | TF-11 | AF483624 | 1425/1493 = 95.4% |
| *Bacillus methanolicu* | NCIMB 13113 | AB112727 | 1418/1494 = 94.9% |
| *Bacillus carboniphilus* | JCM9731 | AB021182 | 1418/1494 = 94.9% |
| *Bacillus oleronius* | DSM 9356 | X82492 | 1422/1504 = 94.5% |
| *Bacillus sporothermodurans* | M215 | U49078 | 1412/1488 = 94.9% |
| *Bacillus firmus* | IAM 12464 | D16268 | 1408/1487 = 94.7% |
| *Bacillus humi* | LMG 22167 | AJ627210 | 1410/1492 = 94.5% |
| *Bacillus cereus* | ATCC 14579 | NC_004722 | 1412/1504 = 93.9% |
| *Bacillus pseudofirmus* | DSM8715 | X76439 | 1406/1949 = 94.1% |
| *Bacillus halodurans* | DSM 497 | AJ302709 | 1412/1501 = 94.1% |
| *Bacillus algicola* | KMM 3737 | AY228462 | 1420/1513 = 93.9% |
| *Bacillus anthracis* | Ames | NC_003997 | 1400/1490 = 94.0% |
| *Bacillus flexus* | IFO15715 | AB021185 | 1413/1508 = 93.7% |
| *Bacillus weihenstephanensis* | DSM11821 | AB021199 | 1410/1507 = 93.6% |

TABLE 1-continued

| Registered name | Strain name | Accession No. | Homology |
|---|---|---|---|
| Bacillus jeotgali | YKJ-10 | F221061 | 1404/1494 = 94.0% |
| Bacillus hwajinpoensis | SW-72 | AF541966 | 1404/1495 = 93.9% |

TABLE 2

| Registered name | Strain name | Accession No. | Homology |
|---|---|---|---|
| Bacillus sp. | TUT1206 | AB188212 | 1509/1510 = 99.9% |
| Bacillus subtilis | | AB110598 | 1509/1510 = 99.9% |
| Bacillus subtilis | | AB177641 | 1510/1510 = 100.0% |
| Bacillus subtilis | | AB065370 | 1508/1510 = 99.9% |
| Bacillus subtilis | IDCC1105 | AY995572 | 1506/1507 = 99.9% |
| Bacillus subtilis | IDCC1103 | AY995570 | 1506/1507 = 99.9% |
| Bacillus subtilis | IDCC1102 | AY995569 | 1506/1507 = 99.9% |
| Bacillus subtilis | IDCC1101 | AY995568 | 1506/1507 = 99.9% |
| Bacillus licheniformis | HDM02 | DQ167473 | 1508/1510 = 99.9% |
| Bacillus subtilis | YYW-1 | DQ017585 | 1508/1510 = 99.9% |
| Bacillus licheniformis | | AY971527 | 1508/1510 = 99.9% |
| Bacillus subtilis | IAM 12118 | AB024061 | 1508/1510 = 99.9% |
| Bacillus sp. | X3 | AY160223 | 1507/1510 = 99.8% |
| Bacillus subtilis | DSM10 | AJ276351 | 1500/1501 = 99.9% |
| Bacillus subtilis | IDCC1104 | AY995571 | 1506/1508 = 99.9% |
| Bacillus subtilis | | DQ198162 | 1498/1499 = 99.9% |
| Bacillus subtilis | | AY601722 | 1498/1499 = 99.9% |
| Bacillus subtilis | AHU 1035 | AB215103 | 1501/1503 = 99.9% |
| Bacillus subtilis | CCM 1999 | DQ207730 | 1506/1510 = 99.7% |
| Bacillus subtilis | 168 | D88802 | 1506/1510 = 99.7% |
| Bacillus subtilis | BWDY-4 | DQ314533 | 1503/1507 = 99.7% |
| Bacillus subtilis | MO7 | AY553100 | 1490/1491 = 99.9% |
| Bacillus subtilis | N10;BGSC 3A17 | AF318900 | 1499/1503 = 99.7% |
| Bacillus subtilis | 168 | D84213 | 1507/1511 = 99.7% |
| Bacillus sp. | CH10-1 | AB055853 | 1490/1491 = 99.9% |
| Bacillus sp. | CH7-1 | AB055852 | 1490/1491 = 99.9% |
| Bacillus sp. | CH20-1 | AB055851 | 1490/1491 = 99.9% |
| Bacillus sp. | CH19-3 | AB055850 | 1490/1491 = 99.9% |
| Bacillus sp. | CH15-2 | AB055849 | 1490/1491 = 99.9% |
| Bacillus sp. | CH4-5 | AB055848 | 1490/1491 = 99.9% |

The 104-1-3-1 strain is a subspecies of *Bacillus subtilis* shown in Table 3 below. 16S rDNA derived from each of the type strains of 8 species and 1 subspecies including very closely related *Bacillus subtilis* subsp. *spizizenii*, which constitutes the same cluster thereas, and two relatively related species (out-group) was obtained and subjected to molecular phylogenetic analysis. In this context, T at the end of each strain name represents a type strain of the species.

TABLE 3

| Species name | Strain name | Accession No. |
|---|---|---|
| Bacillus amyloliquefaciens | ATCC23350[T] | X60605 |
| Bacillus atrophaeus | JCM9070[T] | AB021181 |
| Bacillus axarquiensis | CR-119[T] | AY603657 |
| Bacillus licheniformis | DSM13[T] | X68416 |
| Bacillus malacitensis | CR-95[T] | AY603656 |
| Bacillus mojavensis | IFO15718[T] | AB021191 |
| Bacillus sonorensis | NRRL_B-23154[T] | AF302118 |
| Bacillus subtilis | IAM12118[T] | AB042061 |
| Bacillus subtilis subsp. spizizenii | NRRL_B-23049[T] | AF074970 |
| Bacillus vallismortis | DSM11031[T] | AB021198 |
| Bacillus velezensis | CR-502[T] | AY603658 |

In addition, the nucleotide sequences of the type strains shown in Table 3 were aligned with the nucleotide sequence of the 104-1-3-1 strain according to CLUSTAL W (J. D. Thompson et al., 1994, Nucleic Acids Research, 22, pp. 4673-4680). A phylogenetic tree shown in FIG. 2 was prepared using phylogenetic tree preparation software MEGA ver3.1 (S. Kumar, K. 2004, Briefings in Bioinformatics, 5, pp. 150-163). The neighbor-joining method (N. Saitou and M. Nei, 1987, Molecular Biology and Evolution, 4, pp. 406-425) was used in phylogenetic tree prediction. The reliability of each phylogenetic branch indicated by numerical value in each branch of FIG. 2 was evaluated by the bootstrap method (J. Felsenstein, 1985, Evolution, 39, 783-791).

Figure 2:
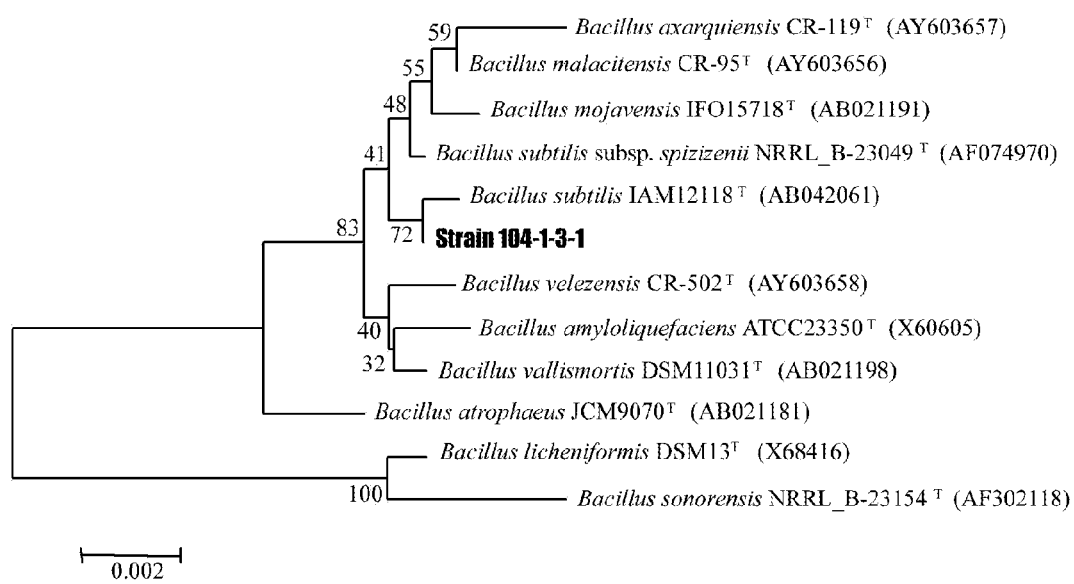
FIG. 2 shows the molecular phylogenetic tree of the 104-1-3-1 strain based on 16S rDNA. The lower left line denotes a scale bar. T at the end of each strain name represents a type strain of the species.

As a result, as shown in FIG. 2, the 16S rDNA of the 104-1-3-1 strain was included in a phylogenetic branch with *Bacillus subtilis* 16S rDNA and thus presumed to belong to *Bacillus subtilis*.

Morphological Observation and Tests on Physiological and Biochemical Properties

The 104-1-3-1 strain was cultured at 30° C. for 24 hours in a medium (Nutrient agar, manufactured by Becton, Dickinson and Company).

The cultured 104-1-3-1 strain was gram-stained (Favor G, manufactured by Nissui Pharmaceutical Co., Ltd.) and observed both morphologically and in a gram-stained manner under an optical microscope (BX50F4, manufactured by Olympus Corp.).

Also, physiological and biochemical tests including catalase reaction, oxidase reaction, acid/gas production from glucose, and oxidative/fermentative glucose (O/F) tests were conducted using API50CH (manufactured by bioMerieux SA).

The results of morphological observation and tests on physiological and biochemical properties are shown in Tables 4 to 6 below. In Tables 4 to 6, "+" represents positive, and, "−" represents negative.

As shown in Table 4 below, the 104-1-3-1 strain was a gram-positive *bacillus* that grows under aerobic conditions. This strain exhibited a chain of cells and formed spores. The swelling of the bacterial spores was not observed. The strain was found positive for catalase reaction and negative for oxidase reaction.

As shown in Tables 5 and 6 below, the 104-1-3-1 strain oxidized L-arabinose, ribose, and glucose, etc. and did not oxidize erythritol, D-arabinose, and L-xylose, etc., in the API test. As shown in Table 4 below, the strain did not grow under anaerobic conditions and grew at 50° C. and in a medium containing 10% NaCl. The strain hydrolyzed casein, but did not hydrolyze starch.

TABLE 4

| Cellular morphology | | *Bacillus* with chain of cells (1.0 μm × 2.0 μm to 3.0 μm) |
|---|---|---|
| Gram staining | | + |
| Presence or absence of spore | | + |
| Mobility | | − |
| Colonial morphology | Diameter | 2.0 mm to 3.0 mm |
| | Color tone | Cream color |
| | Shape | Round |
| | Elevation | Lens-shaped |
| | Margin | Wavy |
| | Surface shape | Rough |
| | Transparency | Opaque |
| | Texture | Butyrous |

TABLE 4-continued

| Cellular morphology | | *Bacillus* with chain of cells (1.0 μm × 2.0 μm to 3.0 μm) |
|---|---|---|
| Culture temperature | 37° C. | + |
|  | 45° C. | + |
|  | 50° C. | + |
| Catalase reaction | | + |
| Oxidase reaction | | − |
| Acid/gas production from glucose | | −/− |
| Oxidative/fermentative (O/F) test | | −/− |
| Growth in medium containing 10% NaCl | | + |
| Growth under anaerobic condition | | − |
| Casein hydrolysis | | + |
| Starch hydrolysis | | − |

TABLE 5

| Biochemical test | |
|---|---|
| β-galactosidase | + |
| Arginine dihydrolase | − |
| Lysine decarboxylase | − |
| Ornithine decarboxylase | − |
| Utilization of citric acid | + |
| Hydrogen sulfide production | − |
| Urease | − |
| Tryptophan deaminase | − |
| Indole production | − |
| Acetoin production (VP) | + |
| Gelatinase | + |
| Sulfate reduction | + |

TABLE 6

| Oxidative test | | | |
|---|---|---|---|
| Control | − | Esculin | + |
| Glycerol | + | Salicin | − |
| Erythritol | − | Cellobiose | − |
| D-arabinose | − | Maltose | + |
| L-arabinose | + | Lactose | − |
| Ribose | + | Melibiose | − |
| D-xylose | − | Sucrose | + |
| L-xylose | − | Trehalose | + |
| Adonitol | − | Inulin | + |
| β-methyl-D-xylose | − | Melicitose | − |
| Galactose | − | Raffinose | − |
| Glucose | + | Starch | − |
| Fructose | + | Glycogen | − |
| Mannose | + | Xylitol | − |
| Sorbose | − | Gentiobiose | − |
| Rhamnose | − | D-turanose | − |
| Dulcitol | − | D-lyxose | − |
| Inositol | + | D-tagatose | − |
| Mannitol | + | D-fucose | − |
| Sorbitol | + | L-fucose | − |
| α-methyl-D-mannoside | − | D-arabitol | − |
| α-methyl-D-glucoside | + | L-arabitol | − |
| N-acetylglucosamine | − | Gluconate | − |
| Amygdalin | − | 2-ketogluconic acid | − |

These properties were confirmed by 16S rDNA analysis and molecular phylogenetic analysis to be partially similar to those of *Bacillus subtilis* to which the 104-1-3-1 strain was presumed to belong, whereas a lack of arbutin, salicin, cellobiose, starch, and glycogen oxidations differed from the typical properties of *Bacillus subtilis*. From these results, the 104-1-3-1 strain was presumed to be a novel strain of *Bacillus* sp.

The 104-1-3-1 strain was deposited under Accession No: NITE BP-680 with National Institute of Technology and Evaluation (2-5-8 Kazusakamatari, Kisarazu-shi, Chiba, 292-0818 Japan) on Nov. 21, 2008.

Test Example 3

Influence of Culture Temperature of 104-1-3-1 Strain on Protease Activity

The 104-1-3-1 strain was added to a liquid medium (pH 6.2) containing 2.5% by mass of a defatted soybean component (product name: Toast Soya, manufactured by Nisshin Oillio Group, Ltd.), 6.0% by mass of sucrose (manufactured by Wako Pure Chemical Industries, Ltd.), 0.1% by mass of potassium hydrogen phosphate (manufactured by Wako Pure Chemical Industries, Ltd.), and 0.2% of calcium carbonate (manufactured by Wako Pure Chemical Industries, Ltd.) and shake-cultured at each temperature of 27° C., 30° C., 35° C., and 40° C. After a lapse of 0 hours, 24 hours, 41 hours, and 65 hours into the culture, the bacterial cells of the 104-1-3-1 strain were removed by centrifugation. The protease activity of each culture supernatant containing extracellularly produced protease was determined by a modification of the method described in C. E. McDonald and Lora L. Chen, "The Lowry Modification of the Folin Reagent for Determination of Proteinase Activity", Analytical Biochemistry, (1965), 10, 175-177, i.e., by the following method:

5 mL of 2% by mass of a milk casein solution was collected into each test tube (18 mm×180 mm) and incubated for 3 minutes in a thermostat bath of 40° C. Next, when the temperature of this 2% by mass of the milk casein solution reached 40° C., 1 mL of each culture supernatant of the 104-1-3-1 strain was added thereto. After reaction thereof at 40° C. for 10 minutes, the reaction was terminated by the addition of 5 mL of a protein precipitant (19.5 mL of acetic acid, 18 g of sodium acetate (anhydrous) (manufactured by Wako Pure Chemical Industries, Ltd.), and 18 g of trichloroacetic acid (manufactured by Wako Pure Chemical Industries, Ltd.) were separately dissolved in 300 mL of distilled water and then mixed to adjust the total amount to 1,000 mL). After the termination of the reaction, the reaction solution was kept as it was at 40° C. in the thermostat bath for 30 minutes and then naturally filtered through Filter Paper No. 2 (manufactured by ADVANTEC, Toyo Roshi Kaisha, Ltd.). Then, 2 mL of this filtrate was collected into another test tube, to which 5 mL of a 0.5 M sodium carbonate (manufactured by Wako Pure Chemical Industries, Ltd.) solution and then 1 mL of a 3-fold diluted Folin's reagent (product name: Phenol Test Solution, manufactured by Nacalai Tesque, Inc.) were added and mixed. The resulting mixture was incubated for 30 minutes in a thermostat bath of 40° C. Immediately after a lapse of 30 minutes, the absorbance was measured at a wavelength of 660 nm using a spectrophotometer and represented by T.

The blank value of absorbance was measured by the same operation as in the protease activity assay on the culture supernatant of the 104-1-3-1 strain except that the culture supernatant of the 104-1-3-1 strain was not added, and, instead, 5 mL of the protein precipitant was added to 5 mL of 2% by mass of a milk casein solution incubated at 40° C. and sufficiently mixed, followed by the addition of 1 mL of the liquid medium (pH 6.2). This blank value was represented by B.

The protease activity was calculated according to equation 1 below from the absorbance (T) of the 104-1-3-1 strain culture supernatant and the blank value (B). The unit of the activity thus calculated is referred to as "FLV" (see C. E. McDonald and Lora L. Chen, "The Lowry Modification of the Folin Reagent for Determination of Proteinase Activity", Analytical Biochemistry, (1965), 10, 175-177).

$$\text{Protease activity (FLV)}=[(T-B)\times 66.7\div 2]\times \text{Culture supernatant dilution ratio} \quad \text{(equation 1)}$$

Figure 3:
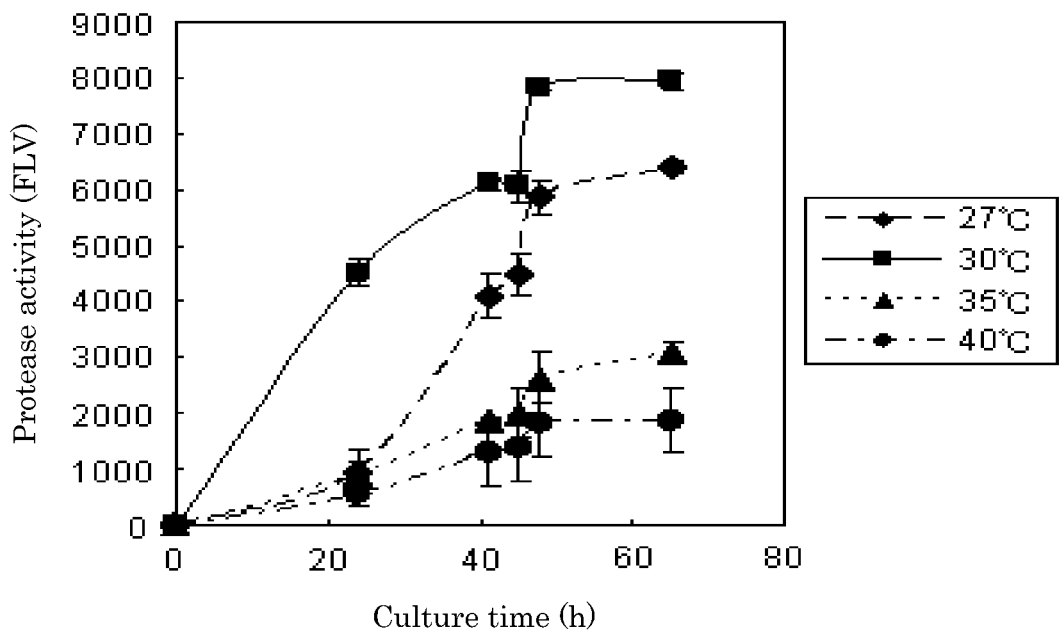
FIG. 3 is a diagram showing the relationship between the culture temperature of the 104-1-3-1 strain and the activity of a thrombolytic enzyme extracellularly produced by the 104-1-3-1 strain along with culture in Test Example 3. The ordinate denotes thrombolytic enzyme activity (FLV). The abscissa denotes the incubation time (h) of a culture supernatant. The "filled rhomboid" represents the results obtained at a culture temperature of 27° C. The "filled square" represents the results obtained at a culture temperature of 30° C. The "filled triangle" represents the results obtained at a culture temperature of 35° C. The "filled circle" represents the results obtained at a culture temperature of 40° C. The plot in the graph represents a mean of 3 measurements±standard deviation.

The results are shown in FIG. 3. The plot in the graph represents a mean of 3 measurements of 104-1-3-1 strain-derived protease activity at each temperature±standard deviation.

As seen from the results of FIG. 3, the 104-1-3-1 strain produced protease in the largest amount and thus exhibited the highest protease activity, when cultured at 30° C. It was also confirmed that a longer culture time offered higher protease activity.

Test Example 4

Study on Optimum Temperature for Protease

The 104-1-3-1 strain was added to the same liquid medium (pH 6.2) as in Test Example 3 and cultured at 30° C. for 72 hours. Then, the bacterial cells were removed by centrifugation to obtain a protease-containing culture supernatant. This culture supernatant of the 104-1-3-1 strain was heated at each temperature of 40° C., 43° C., 47° C., 50° C., and 53° C. for each time of 0 hours, 1 hour, 2 hours, and 3 hours and rapidly cooled.

The protease activity was measured in the same way as in Test Example 3 except that: each culture supernatant prepared in Test Example 4 was used instead of the culture supernatant of the 104-1-3-1 strain prepared in Test Example 3; and the temperature of the reaction between milk casein and the culture supernatant was changed from 40° C. to a temperature (each of 40° C., 43° C., 47° C., 50° C., and 53° C.) corresponding to the heating temperature of the culture supernatant.

Figure 4:
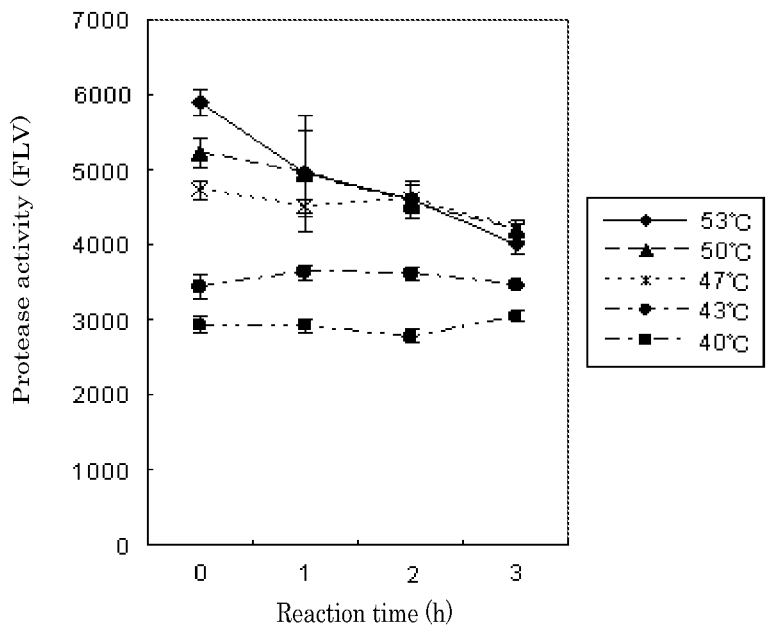
FIG. 4 is a diagram showing the optimum temperature for a thrombolytic enzyme produced by the 104-1-3-1 strain and temperature stability in Test Example 4. The ordinate denotes thrombolytic enzyme activity (FLV). The abscissa denotes reaction time (h). The "filled rhomboid" represents the results obtained at a reaction temperature of 53° C. The "filled triangle" represents the results obtained at a reaction temperature of 50° C. The "x-mark" represents the results obtained at a reaction temperature of 47° C. The "filled circle" represents the results obtained at a reaction temperature of 43° C. The "filled square" represents the results obtained at a reaction temperature of 40° C. The plot in the graph represents a mean of 3 measurements±standard deviation.

The results are shown in FIG. 4. As seen from the results of FIG. 4, a higher heating temperature offered higher protease activity in the case of each temperature within the temperature range of 40° C. to 53° C. and an incubation time of 0 hours. For example, the protease activity obtained from heating at 40° C. was approximately half the protease activity obtained from heating at 53° C. It was also confirmed that protease placed under a higher heating temperature exhibited greater reduction in its enzyme activity after 3 hours.

Test Example 5

Study on pH Stability

The 104-1-3-1 strain was added to the same liquid medium (pH 6.2) as in Test Example 3 and cultured at 30° C. for 72 hours. Then, the bacterial cells were removed by centrifugation to obtain a protease-containing culture supernatant. This culture supernatant of the 104-1-3-1 strain was mixed with each buffer solution in equal amounts to adjust the pH to 3, 4, 5, 6, 7, 8, 9, 10, 11, and 12 (buffer solution: 50 mM citric acid-phosphoric acid buffer solution for pH 3 to 6, 50 mM tris-HCl buffer solution for pH 7 to 9, and 50 mM glycine-sodium hydroxide buffer solution for pH 10 to 12). The resulting mixture was incubated at 10° C. for 24 hours. Then, the pH of the solution was adjusted to 7.

The protease activity was measured in the same way as in Test Example 3 except that each culture supernatant prepared in Test Example 5 was used instead of the culture supernatant of the 104-1-3-1 strain prepared in Test Example 3.

Figure 5:
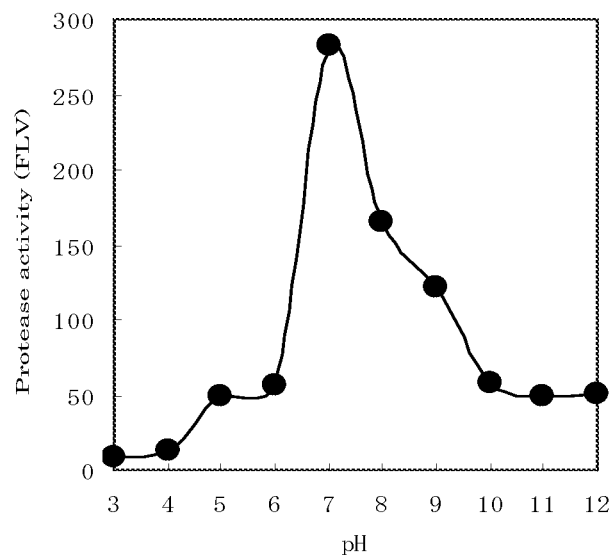
FIG. 5 is a diagram showing the pH stability of a thrombolytic enzyme produced by the 104-1-3-1 strain in Test Example 5. The ordinate denotes thrombolytic enzyme activity (FLV). The abscissa denotes the pH of a culture supernatant.

The results are shown in FIG. 5. The results of FIG. 5 demonstrated that the 104-1-3-1 strain-derived protease is most stable at pH 7. Its activity was extremely reduced at a strongly acidic pH, whereas 15% of the activity at pH 7 remained at a strongly alkaline pH.

Test Example 6

Freeze-Drying Stability of Protease

The 104-1-3-1 strain was added to the same liquid medium (pH 6.2) as in Test Example 3 and cultured at 30° C. for 72 hours. Then, the bacterial cells were removed by centrifugation to obtain a protease-containing culture supernatant. 8 L of this culture supernatant of the 104-1-3-1 strain was used and freeze-dried in a freeze-dryer manufactured by Virtis, Inc. The resulting freeze-dried powder was pulverized. Then, 0.1 mg of this powder was dissolved in 5 mL of a phosphoric acid buffer solution (50 mM, pH 7) and stored overnight at 4° C. The protease activity of this powder solution was determined in the same way as in Test Example 3 and compared with that before freeze-drying. The protease activity was calculated as activity per 10 L of the culture supernatant.

Figure 6:
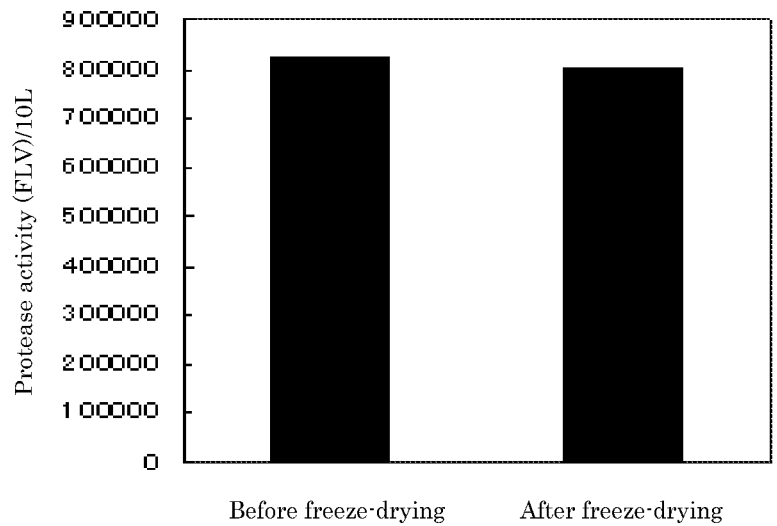
FIG. 6 is a diagram showing the freeze-drying stability of a thrombolytic enzyme in Test Example 6. The ordinate denotes thrombolytic enzyme activity (FLV).
Figure 7A:
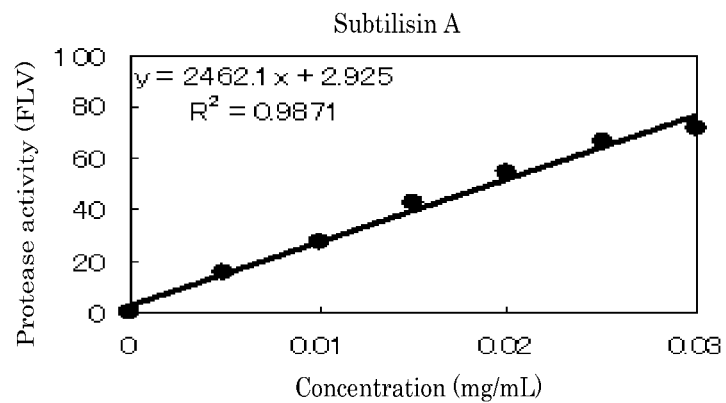
FIG. 7A is a calibration curve showing the correlation of the enzyme activity (FLV) of subtilisin A against casein as a substrate to each concentration.
Figure 7B:
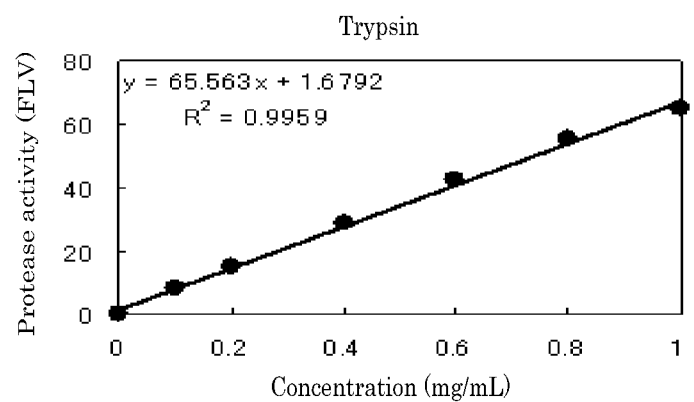
FIG. 7B is a calibration curve showing the correlation of the enzyme activity (FLV) of trypsin against casein as a substrate to each concentration.
Figure 7C:
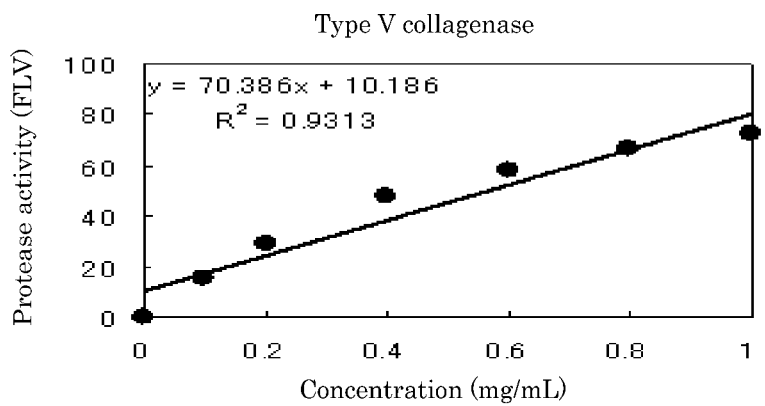
FIG. 7C is a calibration curve showing the correlation of the enzyme activity (FLV) of type V collagenase against casein as a substrate to each concentration.
Figure 7D:
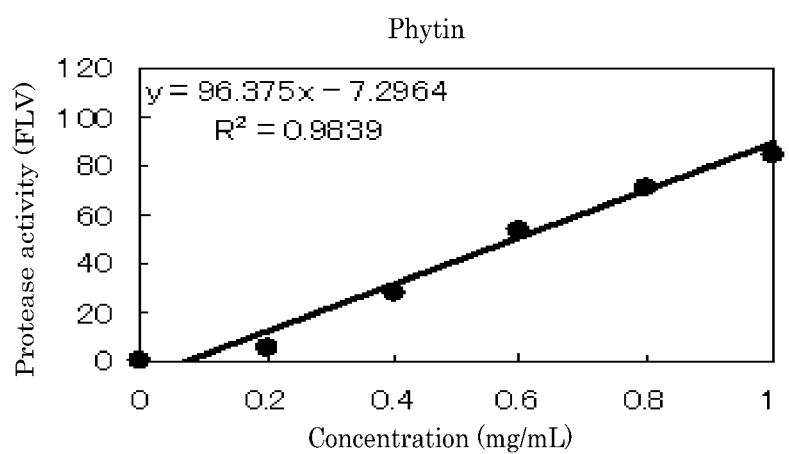
FIG. 7D is a calibration curve showing the correlation of the enzyme activity (FLV) of phytin against casein as a substrate to each concentration.

The results are shown in FIG. 6. The results of FIG. 6 demonstrated that the 104-1-3-1 strain-derived protease exhibits substantially no reduction in its activity even after freeze-drying and can be stored in the form of a powder smaller in volume than a solution.

Test Example 7

Study on Fibrinolytic (Thrombolytic) Activity of 104-1-3-1 Strain-Derived Protease The protease-containing culture supernatant of Test Example 6 before freeze-drying was dialyzed against a potassium phosphate buffer solution (50 mM, pH 7) and then freeze-dried in the same way as in Test Example 6. The obtained powder was pulverized. 0.1 mg of the resulting partially purified protease was dissolved in 5 mL of a phosphoric acid buffer solution (50 mM, pH 7), and this solution was used to study its lytic activity against a resistant protein fibrin as a substrate.

Likewise, a serine thrombolytic enzyme subtilisin A (EC3.4.21.14, manufactured by MP Biomedicals, LLC (USA)), a serine thrombolytic enzyme trypsin (EC3.4.21.4, manufactured by Wako Pure Chemical Industries, Ltd.), a cysteine thrombolytic enzyme phytin (EC3.4.22.3, manufactured by MP Biomedicals, LLC (USA)), and a metallo thrombolytic enzyme type V collagenase (EC3.4.24.3, manufactured by Wako Pure Chemical Industries, Ltd.) were used. A group supplemented with none of these thrombolytic enzymes was used as a control group.

Preparation of Enzyme Solution

The enzyme activity (FLV) of the partially purified protease solution was determined in the same way as in Test Example 3 and thereby confirmed to be 111.

In order to equalize conditions for the enzyme activity (FLV=111) of the partially purified protease solution and for the enzyme activities of various proteases described above, comparative study was conducted on the enzyme activities of these various proteases against casein.

Each enzyme activity was determined and evaluated in the same way as in Test Example 3 using these various proteases at concentrations shown below as the protease of Test Example 3. As shown below, serial dilutions of each of these proteases were prepared, and a calibration curve of enzyme activity versus protease concentration was prepared for each protease. The concentration of each protease at which the protease exhibits arbitrary enzyme activity can be determined by calculation from the thus-prepared calibration curve of enzyme activity against casein as a substrate versus protease concentration. The calibration curves are shown in FIGS. 7A to 7D.

[Type and Concentration of Enzyme]

Subtilisin A: 0.005 mg/mL, 0.01 mg/mL, 0.015 mg/mL, 0.02 mg/mL, 0.025 mg/mL, and 0.03 mg/mL Trypsin: 0.1 mg/mL, 0.2 mg/mL, 0.4 mg/mL, 0.6 mg/mL, 0.8 mg/mL, and 1.0 mg/mL Type V collagenase: 0.1 mg/mL, 0.2 mg/mL, 0.4 mg/mL, 0.6 mg/mL, 0.8 mg/mL, and 1.0 mg/mL Phytin: 0.2 mg/mL, 0.4 mg/mL, 0.6 mg/mL, 0.8 mg/mL, 1.0 mg/mL, and 1.2 mg/mL Preparation of Fibrin-Containing Solid Medium The fibrin-containing solid medium was prepared by the following method according to composition shown below: a lower layer was dispensed to 9-cm plates and solidified. Subsequently, 10 units of thrombin (manufactured by Ito Life Science Co., Ltd.), 0.02 M calcium chloride, a 0.05 M borax buffer solution (pH 8.5) (1 mL) were dispensed to the plates. Further, an agarose solution and a fibrinogen solution were simultaneously dispensed thereto to prepare the solid medium.

—Composition of Fibrin-Containing Solid Medium—

[1.5% By Mass of Agar (Lower Layer)]

Difco agar (manufactured by Difco Laboratories, Inc.) 1.5% by mass

[2% By Mass of Agarose and 0.6% by Mass of Fibrin (Upper Layer)]

Agarose (dissolved in distilled water) 2.0% by mass

Fibrinogen (dissolved in a 0.05 M borax buffer solution (pH 8.5); manufactured by Ito Life Science Co., Ltd.) 0.6% by mass Fibrinolytic Activity Assay A filter paper having a diameter of 8 mm (8 mm thick, paper disk for antibiotic assay, manufactured by Toyo Roshi Kaisha, Ltd) was placed on the upper layer of the fibrin-containing solid medium, impregnated with 80 μL of each protease solution prepared with protease activity (FLV) of 111, and left standing overnight at 37° C. Then, the diameter of a digestion circle (circle in which fibrin was lysed) was measured.

Figure 8:
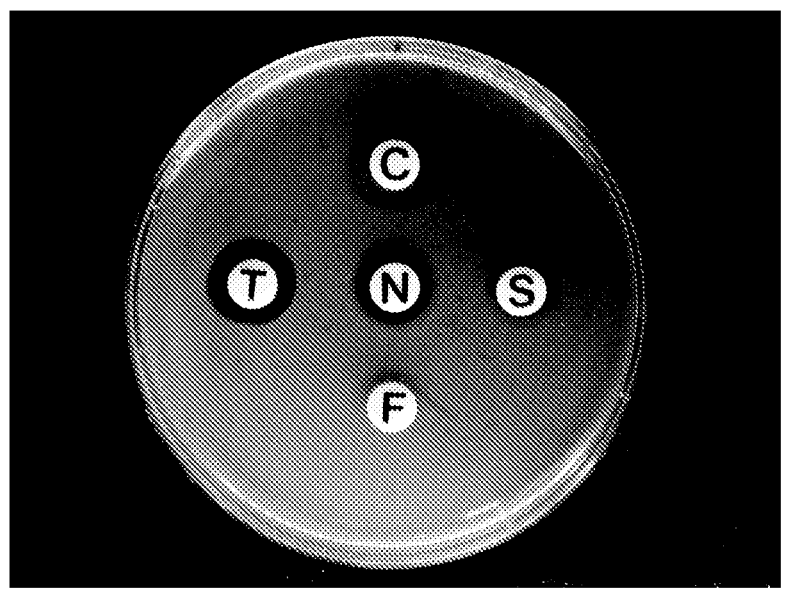
FIG. 8 is a diagram showing the ability of various enzymes to decompose fibrin in Test Example 7. "N" represents nattokinase. "S" represents subtilisin A. "T" represents trypsin. "C" represents type V collagenase. "F" represents phytin.

The results are shown in FIG. 8. As seen from these results, a distinct digestion circle was observed for the 104-1-3-1 strain-derived protease (indicated by "N" in FIG. 8), demonstrating that this protease is a thrombolytic enzyme having thrombolytic activity.

As for the control groups, a digestion circle was observed for trypsin (indicated by "T" in FIG. 8), whereas no digestion circle was seen for subtilisin A (indicated by "S" in FIG. 8), type V collagenase (indicated by "C" in FIG. 8), and phytin (indicated by "F" in FIG. 8).

Thus, the 104-1-3-1 strain-derived thrombolytic enzyme was shown to have unique substrate-decomposing properties in the decomposition of a resistant protein such as fibrin.

Test Example 8

Purification of Thrombolytic Enzyme

The thrombolytic enzyme in the culture supernatant of the 104-1-3-1 strain was purified by the following method: first, the 104-1-3-1 strain was added to the same liquid medium (pH 6.2) as in Test Example 3 and cultured at 30° C. for 72 hours. Then, the bacterial cells were removed by centrifugation to obtain a thrombolytic enzyme-containing culture supernatant. A thrombolytic enzyme-containing fraction was separated from this culture supernatant of the 104-1-3-1 strain by hydrophobic interaction chromatography and then desalted by gel filtration chromatography. The desalted thrombolytic enzyme-containing fraction was purified by density gradient isoelectric focusing.

Fractionation by Hydrophobic Interaction Chromatography

The hydrophobic interaction chromatography was performed under the following conditions:

Column: prepacked column (Hi-Trap 16/10 Phenyl FF high, manufactured by Bio-Rad Laboratories, Inc.)

Apparatus: BioLogic DuoFlow system (manufactured by Bio-Rad Laboratories, Inc.)

Solvent: solution A: 30% by volume of 2-propanol+0.05 M phosphoric acid buffer solution (pH 7), solution B: 1 M ammonium sulfate+0.05 M phosphoric acid buffer solution (pH 7)

Added amount: 1 mL

Flow rate: 2 mL/min

Figure 9:
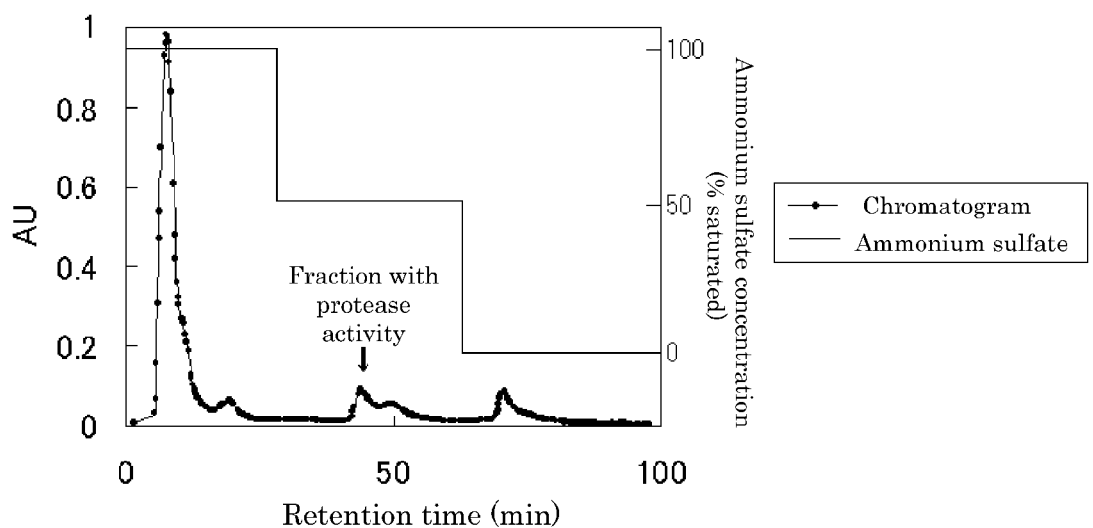
FIG. 9 is a diagram showing results of fractionating the culture supernatant of the 104-1-3-1 strain by hydrophobic interaction chromatography in Test Example 8. The chromatogram of FIG. 9 shows results of separating fractions with proteolytic activity from a 104-1-3-1 strain culture liquid by hydrophobic interaction chromatography.

FIG. 9 shows the chromatogram of the hydrophobic interaction chromatography and change in ammonium sulfate concentration. All fractions shown in the chromatogram of FIG. 9 were collected.

The thrombolytic enzyme was measured in the same way as in Test Example 3 except that the fractions were used instead of the culture supernatant of the 104-1-3-1 strain prepared in Test Example 3.

As a result, thrombolytic enzyme activity was confirmed in peak fractions indicated by arrow in FIG. 9 (fraction 39 to fraction 43).

Desalting by Gel Filtration Chromatography

The fractions with thrombolytic enzyme activity thus confirmed by the hydrophobic interaction chromatography were desalted using PD-10 columns (manufactured by GE Healthcare Japan Corp.) and purified by density gradient isoelectric focusing shown below.

Purification by Density Gradient Isoelectric Focusing

Each fraction with thrombolytic enzyme activity was fractionated using Bio-Lyte (3/10 and 7/9) (manufactured by Bio-Rad Laboratories, Inc.) as a carrier ampholyte (concentration: 40%) and a glycerin density gradient isoelectric focusing apparatus (column volume: 90 mL, model N-1720, manufactured by Nihon Eido Corp.). Electrophoresis was conducted for 72 hours with the voltage set to 600 V. A density gradient was created using 50% by mass of sucrose.

The thrombolytic enzyme was measured in the same way as in Test Example 3 except that each fraction obtained by the density gradient isoelectric focusing was used instead of the culture supernatant of the 104-1-3-1 strain prepared in Test Example 3. Also, the pH of each fraction was measured.

Figure 10:
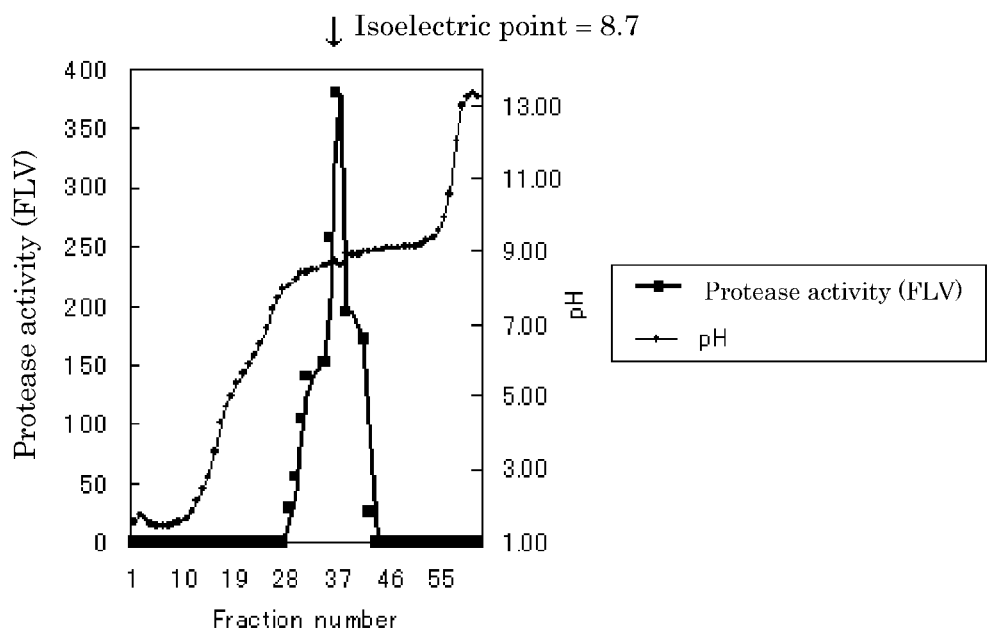
FIG. 10 is a diagram showing results of fractionating the culture supernatant of the 104-1-3-1 strain by hydrophobic interaction chromatography and then further fractionating desalted thrombolytic enzyme-containing fractions by density gradient isoelectric focusing in Test Example 8. The ordinate denotes thrombolytic enzyme activity (FLV). The abscissa denotes fraction number from density gradient isoelectric focusing.

FIG. 10 shows the chromatogram of the density gradient isoelectric focusing and the results of pH measurement. The fraction shown in FIG. 10 to have the highest thrombolytic enzyme activity (fraction 35) had an isoelectric point of 8.7. This represents the isoelectric point of the 104-1-3-1 strain-derived thrombolytic enzyme.

Confirmation of Molecular Weight of Thrombolytic Enzyme 50 ng of a protein component in the fraction (fraction 35) was mixed with 13 μL of a dithioerythritol-containing Laemmli buffer solution (0.125 M Tris-HCl [pH 6.8], 10% glycerol, 2% sodium dodecyl sulfate, 0.1 M dithioerythritol, and 0.02% bromophenol blue), treated at 95° C. for 3 minutes, and then subjected to SDS-polyacrylamide gel electrophoresis in the presence of sodium dodecyl sulfate (SDS). The acrylamide concentration of the gel was set to 4% by mass for concentration and to 10% by mass for separation, and the electrophoresis was performed under constant current conditions of 10 mA and 25 mA, respectively. The polyacrylamide gel after the electrophoresis was fixed with a fixing solution (40% by volume of ethanol+10% by volume of acetic acid), then fluorescently stained with Flamingo gel stain (manufactured by Bio-Rad Laboratories, Inc.), and observed under UV excitation using Ultraviolet Transilluminator (manufactured by Funakoshi Corp.).

Figure 11:
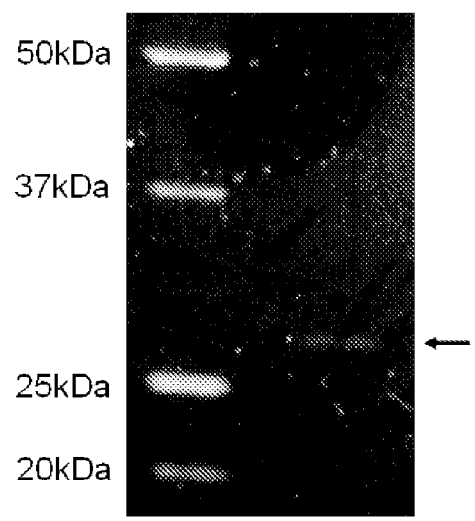
FIG. 11 is a diagram showing results of polyacrylamide electrophoresis of a thrombolytic enzyme purified from a 104-1-3-1 strain culture supernatant in Test Example 8. The left lane denotes a marker. The right lane denotes the band of nattokinase (indicated by arrow).

The results are shown in FIG. 11. As seen from the results of FIG. 11, the protein component of the fraction (fraction 35) produced a single band (indicated by arrow in FIG. 11). The obtained single band had an estimated relative molecular mass of approximately 27,000 Da by mobility comparison with a standard protein sample (marker, Precision Plus Protein Standards, manufactured by Bio-Rad Laboratories, Ltd.).

Test Example 9

Identification of Thrombolytic Enzyme

The single band of the 104-1-3-1 strain-derived thrombolytic enzyme in the polyacrylamide gel of Test Example 8 after electrophoresis was excised and washed with ultrapure water. After reductive alkylation, the enzyme in the gel was digested with trypsin at 37° C. to prepare a peptide solution.

The prepared peptide solution was fractionated by reverse-phase chromatography under the following conditions:
[Reverse-Phase Chromatography]
Column: Magic C18AQ (particle size: 3 µm, pore size: 200 angstroms, column inside diameter: 200 µm, column length: 50 mm; manufactured by Michrom BioResources, Inc.)
Autosampler: CTC-HTS PAL (manufactured by AMR Inc.)
Pump: Paradigm MS4 system (manufactured by AMR Inc.)
Solvent: solution A: 2% by volume of acetonitrile/98% by volume of ultrapure water (containing 0.1% by volume of formic acid), solution B: 90% by volume of acetonitrile/10% by volume of ultrapure water (containing 0.1% by volume of formic acid)
Flow rate: 2 µL/min
Concentration gradient: peptides were eluted over 20 minutes under conditions involving 95% by volume of solution A+5% by volume of solution B and then 55% by volume of solution A+45% by volume of solution B.

The peptides separated by the reverse-phase chromatography were ionized by the nanospray ionization method. The m/z of individual peptides (precursor ions) was measured using a mass spectrometer (LTQ-Orbitrap, manufactured by Thermo Fisher Scientific Inc.). In order to further obtain internal sequence information about the peptides, the peptides were allowed to collide with helium gas in a collision cell, and the m/z of production ions formed by decomposition was measured (MS/MS analysis).

Figure 12:
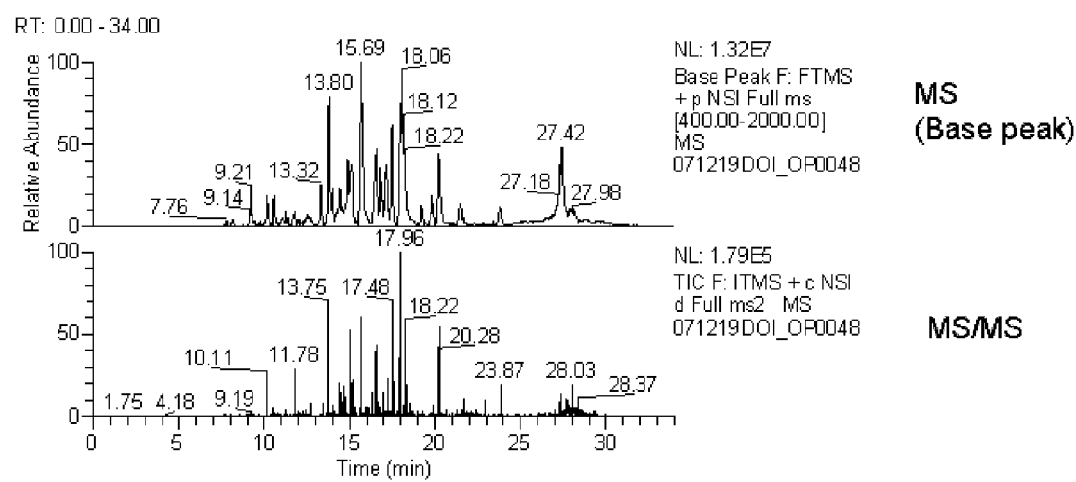
FIG. 12 is a diagram showing spectra of peptides analyzed by liquid chromatography/mass spectrometer in Test Example 9, wherein the peptides were prepared by the trypsin digestion of nattokinase. The ordinate denotes relative ionic strength. The abscissa denotes column retention time. Precursor ions are shown in a base peak chromatogram (upper). Fragment ions in MS/MS analysis are shown in a total ion chromatogram (lower).

The chromatogram is shown in FIG. 12. As seen from the results of FIG. 12, the peptides were favorably separated by liquid chromatography, while MS/MS analysis was successfully conducted. From the measurement value obtained by the mass spectrometer, the thrombolytic enzyme was identified by the MS/MS ion search method using two types of database search engines: Mascot (manufactured by Matrix Science Ltd.) and SEQUEST (BioWorks software, manufactured by Thermo Fisher Scientific Inc.).

From the results of the database search, the 104-1-3-1 strain-derived thrombolytic enzyme was identified as an enzyme belonging to the subtilisin family. The peptides detected by the mass spectrometry occupied 31.8% of the whole amino acid sequence of precursor subtilisin in SEQUEST search. By contrast, the peptides occupied 48% of the amino acid sequence of precursor subtilisin and 30% of the amino acid sequence of active subtilisin in Mascot search.

Test Example 10

Determination of Nucleotide Sequence of Thrombolytic Enzyme Gene

Genomic DNA was extracted from the 104-1-3-1 strain using ISOPLANT kit (manufactured by Nippon Gene Co., Ltd.). In order to amplify the gene of the 104-1-3-1 strain-derived thrombolytic enzyme, the following PCR primers were designed from the upstream and downstream nucleotide sequences of subtilisin genes (Accession Nos: NC_000964, 551909, D00264, and M64743) derived from a plurality of related bacterial species registered in NCBI GenBank: amplification primers having a primer sequence represented by SEQ ID NO: 1 below, which hybridizes to the 20-bp intragenic upstream region of the subtilisin gene, and a primer sequence represented by SEQ ID NO: 2 below, which hybridizes to the 20-bp intragenic downstream region thereof. Conditions for PCR using KOD DNA polymerase (manufactured by Toyobo Co., Ltd.) involved 94° C. for 2 minutes, followed by 30 cycles each involving denaturation at 94° C. for 15 seconds, annealing at 52° C. for 30 seconds, and elongation at 68° C. for 2 minutes. The PCR product having the expected size (up to 1,800 bp) was cloned into a pGEM-T Easy vector (manufactured by Promega Corp.).

```
                                         (SEQ ID NO: 1)
     5'-AGCCATCCGTCGATCATGGA-3'

(SEQ ID NO: 2)
     5'-TAAAATTCCCGATATTGGTT-3'
```

The nucleotide sequence of the cloned gene of the 104-1-3-1 strain-derived thrombolytic enzyme was determined by sequencing using pUC/M13 sequencing primers (forward and reverse primers) in the pGEM-T Easy vector (this sequencing was outsourced to Bio Matrix Research, Inc.). The determined nucleotide sequence was translated into an amino acid sequence (SEQ ID NO: 3). Homology search was performed using NCBI BLASTP.

As a result of the homology search, the amino acid sequence constituting the 104-1-3-1 strain-derived thrombolytic enzyme exhibited 100% identity to the amino acid sequence of the nattokinase gene (Accession No: P35835) registered in GenBank. Thus, the 104-1-3-1 strain-derived thrombolytic enzyme was identified as nattokinase.

As a result of the gene analysis, the 104-1-3-1 strain-derived thrombolytic enzyme is constituted of 275 amino acids and has a relative molecular mass of 27.7. This enzyme exhibits 99.5% and 99.3% homologies to subtilisin E and subtilisin Amylosacchariticus, respectively, which are serine thrombolytic enzymes extracellularly produced by microorganisms belonging to the genus *Bacillus* (see T. Urano et al., 2001, J. Biol. Chem., 27, 24690-24696). The 104-1-3-1 strain-derived thrombolytic enzyme identified by these Test Examples is also referred to as nattokinase.

Test Example 11

Test on Decomposition of Jellyfish

The 104-1-3-1 strain was added to the same liquid medium (pH 6.2) as in Test Example 3 and cultured at 30° C. for 72 hours. Then, the bacterial cells were removed by centrifugation to obtain a nattokinase-containing culture supernatant (pH 7.2). The enzyme activity (FLV) of the nattokinase in this culture supernatant was determined in the same way as in Test Example 3 and thereby confirmed to be 6,500.

Decomposition of *Nemopilema nomurai Kishinouye*

*Nemopilema nomurai Kishinouye* harvested in a fixed net in Maizuru-shi, Kyoto, Japan was used as jellyfish individuals. The individuals of *Nemopilema nomurai Kishinouye* were frozen in dry ice, transported, and then stored at −20° C. Each jellyfish individual was thawed in running water and cut into 5 cm to 10 cm square for the decomposition test.

A beaker was placed on a hot stirrer. 2 L of the nattokinase-containing culture supernatant was added into the beaker and heated to 50° C. A 1-mm mesh basket containing 300 g of *Nemopilema nomurai Kishinouye* was placed in the beaker. The decomposition test was conducted with the contents stirred at a low speed (80 rpm) all the time. The mass of *Nemopilema nomurai Kishinouye* was measured 5 minutes, 10 minutes, 30 minutes, and 60 minutes after the placement of *Nemopilema nomurai Kishinouye* in the culture supernatant. The residual percentage was determined according to equation 2 below. The *Nemopilema nomurai Kishinouye* reacted with the culture supernatant was sampled (4 lineages) at each of the time points, and a mean thereof and standard deviation were determined (hereinafter, this group is also referred to as a "test group").

For a control group, tap water heated to 50° C. was used. Since the culture supernatant subjected to the decomposition of *Nemopilema nomurai Kishinouye* in the test group contained fresh water, fresh water (tap water) was also used in the control group without use of seawater. All the *Nemopilema nomurai Kishinouye* decomposition tests were each conducted three times under the same conditions to confirm reproducibility.

Residual percentage (%)={(Jellyfish mass before decomposition−Jellyfish mass after decomposition)/Jellyfish mass before decomposition}×100     (equation 2)

Figure 13:
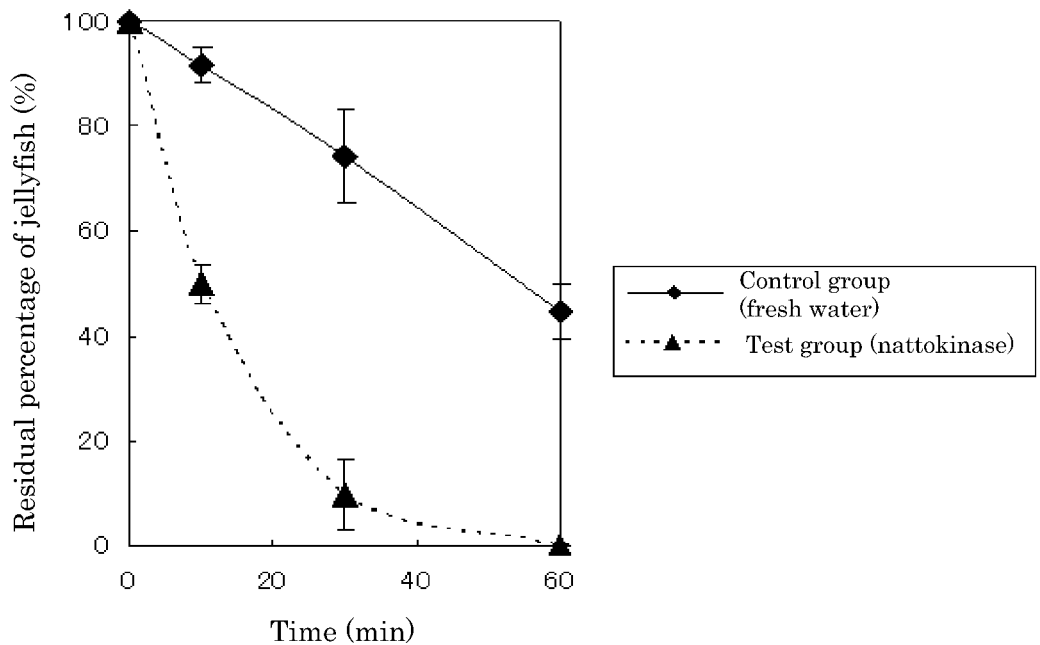
FIG. 13 is a diagram showing change in jellyfish mass caused by the decomposition of *Nemopilema nomurai Kishinouye* with the nattokinase-containing culture supernatant of the 104-1-3-1 strain in Test Example 11. The ordinate denotes the residual percentage of jellyfish (%). The abscissa denotes treatment time (min). The "filled rhomboid" represents a control group. The "filled triangle" represents a test group. The plot in the graph represents a mean of 3 measurements±standard deviation.

The results of the *Nemopilema nomurai Kishinouye* decomposition test are shown in FIG. 13. As seen from the results of FIG. 13, the test group supplemented with the nattokinase-containing culture supernatant was able to completely decompose *Nemopilema nomurai Kishinouye* within 1 hour. By contrast, the control group decomposed only about 50% of *Nemopilema nomurai Kishinouye* when the residual percentage at 0 minutes is compared with that at 60 minutes.

The epidermal portions of the *Nemopilema nomurai Kishinouye* individuals are poorly decomposable. After 30 minutes into the decomposition test, these poorly decomposable epidermal portions remained and thus resulted in high residual percentage. The other portions, however, were completely decomposed within approximately 30 minutes after the start of the test to form a lysate.

These results demonstrated that landed jellyfish individuals as industrial waste can be decomposed in a short time with the minimum energy by nattokinase-mediated jellyfish decomposition.

Decomposition of *Aurelia aurita*
Decomposition of Whole Individual 100 mL of the nattokinase-containing culture supernatant was mixed with 100 mL of a potassium phosphate buffer solution (50 mM, pH 7) in each 300-mL beaker. 3 fresh individuals (whole individuals) of *Aurelia aurita* (bell diameter: approximately 14 cm to 17 cm) were added to the beakers, respectively, and left standing at 30° C. The disappearance of jellyfish morphology was visually observed.

As a result, all the jellyfish individuals were completely decomposed into a liquid state in approximately 2 hours (105 minutes±8 minutes). All the *Aurelia aurita* decomposition tests were each conducted three times under the same conditions to confirm reproducibility.

—Decomposition of Cut Individual—

The decomposition test was conducted under the same conditions as in the decomposition of the whole *Aurelia aurita* individuals except that 100 g of *Aurelia aurita* cut into approximately 3 cm square was used instead of the whole *Aurelia aurita* individuals.

As a result, the cut *Aurelia aurita* was completely decomposed into a liquid state in approximately 65 minutes.

—Control Group—

The decomposition test was conducted under the same conditions as in the decomposition of the whole *Aurelia aurita* individuals except that a liquid mixture of the nattokinase-containing culture supernatant and a potassium phosphate buffer solution (50 mM, pH 7) was autoclaved at 121° C. for 30 minutes, and the resulting liquid mixture with inactivated nattokinase was used instead of the liquid mixture of the nattokinase-containing culture supernatant and the potassium phosphate buffer solution (50 mM, pH 7) in the decomposition of the whole *Aurelia aurita* individuals.

As a result, the decomposition of *Aurelia aurita* was not observed in the control group.

Test Example 12

Study on Nattokinase Concentration for Decomposition of Jellyfish

The 104-1-3-1 strain was added to the same liquid medium (pH 6.2) as in Test Example 3 and cultured at 30° C. for 72 hours. Then, the bacterial cells were removed by centrifugation to obtain a nattokinase-containing culture supernatant (pH 7.2). The enzyme activity (FLV) of the nattokinase in this culture supernatant was determined in the same way as in Test Example 3 and thereby confirmed to be 5,000.

*Chrysaora hysocella*, which is jellyfish living in boreal waters and having a hard, thick body as in the *Nemopilema nomurai Kishinouye*, was harvested, then frozen in dry ice, transported, and then stored at −20° C. Each jellyfish individual was thawed in running water and cut into 5 cm to 10 cm square for the decomposition test.

3 L of water was added to each 5-L beaker and heated to 47° C. using a hot stirrer. After the heating, 1.4 kg of the cut boreal *Chrysaora hysocella* was added to each of the beakers of 4 groups containing the nattokinase-containing culture supernatants at concentrations of 0% by volume, 0.2% by volume, 0.5% by volume, and 1.0% by volume, respectively. Immediately thereafter, each culture liquid was mixed to achieve the predetermined concentration. The liquid mixture containing boreal *Chrysaora hysocella* was kept at 47° C. and reacted with stirring using a magnet stirrer. After a lapse of 2 hours, the mass of boreal *Chrysaora hysocella* residues was measured. The residual percentage with respect to the mass of the boreal *Chrysaora hysocella* added was calculated according to the equation 2 to determine the minimum concentration of the culture supernatant at which the boreal *Chrysaora hysocella* was lysed within 2 hours.

Figure 14:
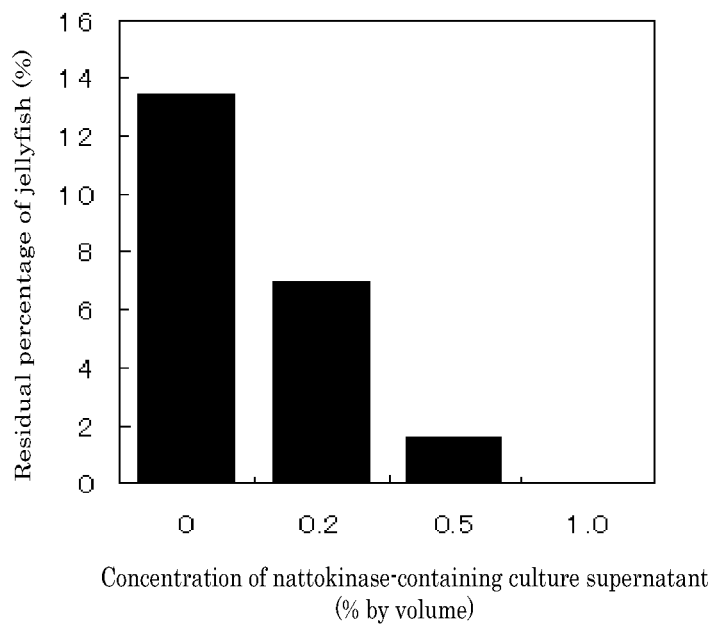
FIG. 14 is a diagram showing change in residual jellyfish mass caused by the decomposition of the whole *Aurelia aurita* individuals with the nattokinase-containing culture supernatant of the 104-1-3-1 strain (thrombolytic enzyme-containing 104-1-3-1 strain culture liquid) in Test Example 11. The ordinate denotes the residual percentage of jellyfish (%). The abscissa denotes the concentration of the nattokinase-containing culture supernatant (% by volume).

The results are shown in FIG. 14. Only heating without adding the nattokinase-containing culture supernatant was able to decrease the mass by approximately 86% (residual percentage: approximately 14%) in 2 hours after the start of the decomposition. This is presumably because the heating dehydrated and thermally denatured the jellyfish. Unlike the addition of the culture supernatant, only the heating failed to completely (100%) decompose the jellyfish, and there remained solid matter that seemed to be thermally denatured.

By contrast, at a culture supernatant concentration of 1.0% by volume, the boreal *Chrysaora hysocella* was substantially completely lysed after approximately 1 hour into the test and completely lysed after 2 hours thereinto.

Test Example 13

Decomposition of *Aurelia aurita* Under Optimum Condition 100 g of *Aurelia aurita* cut into 3 cm square as described in Test Example 11 was added to a 500-mL beaker, to which 300 mL of artificial seawater (Daigo's artificial seawater SP, manufactured by Nihon Pharmaceutical Co., Ltd.) kept at 50° C. was then added. This mixture was mixed with the nattokinase-containing culture supernatant prepared in Test Example 11 so that its enzyme activity (FLV) was 100. The decomposition test was conducted with stirring. The temperature of the *Aurelia aurita* decomposition was set to 50° C., while the pH was set to 8. The *Aurelia aurita* was sampled at each predetermined time point, and change in its mass was determined. The residual percentage was calculated according to equation 2 of Test Example 11 (hereinafter, this group is also referred to as a "test group").

For a control group, artificial seawater kept at 50° C. was used instead of the nattokinase-containing culture supernatant. All the *Aurelia aurita* decomposition tests were each conducted three times under the same conditions to confirm reproducibility.

Figure 15:
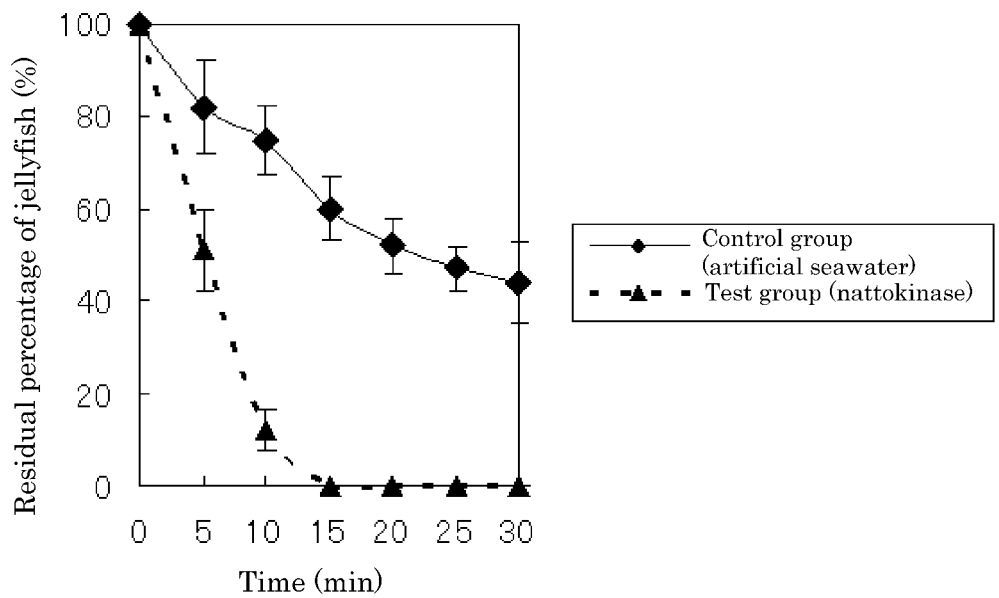
FIG. 15 is a diagram showing change in jellyfish mass caused by the decomposition of *Aurelia aurita* cut into 3 cm square with the nattokinase-containing culture supernatant of the 104-1-3-1 strain (thrombolytic enzyme-containing 104-1-3-1 strain culture liquid) in Test Example 11. The ordinate denotes the residual percentage of jellyfish (%). The abscissa denotes digestion time (min). The plot in the graph represents a mean of 3 measurements standard deviation.

The results are shown in FIG. 15. The plot in the graph represents a mean±standard deviation. As seen from the results of FIG. 15, approximately 40% of the *Aurelia aurita* remained in the control group unmixed with nattokinase after a lapse of 30 minutes.

By contrast, the *Aurelia aurita* was completely lysed into a liquid state within 15 minutes in the nattokinase-supplemented test group.

Test Example 14

Acute Toxicity Test on Decomposed Jellyfish Waste Liquid

The lysate of *Nemopilema nomurai Kishinouye* decomposed using the nattokinase-containing culture supernatant in Test Example 11 was studied for its toxicity according to JIS K0102 (2003) "Testing methods for industrial wastewater", Acute Toxicity Test with Fish (Japanese Standards Association 2003). The law-designated effluent standards for wastewater discharged from power plants are 15 mg/L or less in terms of chemical oxygen demand (COD) values, although the values also differ depending on business establishments.

The COD value of the lysate after the decomposition treatment with the nattokinase-containing culture supernatant was determined using a portable absorptiometer (DR-2400, manufactured by HACH Company) that adheres to Japanese Industrial Standards (JIS), and thereby confirmed to be 1,920 mg/L. This lysate was diluted to 15 mg/L, 30 mg/L, 45 mg/L, 60 mg/L, and 75 mg/L in terms of COD values with seawater to prepare test solutions. *Oryzias latipes* was used as an organism subject to the test. Seawater unmixed with the *Nemopilema nomurai Kishinouye* lysate was used as a control.

Each 5-L fish tank was placed in a laboratory of room temperature (20° C. to 22° C.) and allowed to contain 10 *Oryzias latipes* individuals in each of the test solutions. Under this condition, the fish was raised for 96 hours and observed every 24 hours to count the numbers of live and dead individuals.

The results of determining acute toxicity to *Oryzias latipes* are shown in Table 7 below. The death of *Oryzias latipes* was confirmed in neither the control group nor the test group over 4 days (96 hours). This demonstrated that the diluted lysate of the *Nemopilema nomurai Kishinouye* individuals has no toxicity.

TABLE 7

| | COD value (mg/L) | | | | | |
|---|---|---|---|---|---|---|
| | 0 | 15 | 30 | 45 | 60 | 75 |
| The number of live and dead individuals (the number of dead individuals/the number of live individuals) | 0/10 | 0/10 | 0/10 | 0/10 | 0/10 | 0/10 |

Test Example 15

Comparison of Nattokinase with Other Proteases

Preparation of Enzyme Solution

For nattokinase, the nattokinase-containing culture supernatant of Test Example 6 before freeze-drying was dialyzed against a potassium phosphate buffer solution (50 mM, pH 7) and then freeze-dried in the same way as in Test Example 6. The obtained powder was pulverized. 0.1 mg of the resulting partially purified nattokinase was dissolved in 5 mL of a phosphoric acid buffer solution (50 mM, pH 7). This solution was used as an enzyme solution. The enzyme activity (FLV) of this nattokinase solution was determined in the same way as in Test Example 3 and thereby confirmed to be 14,952.

Subtilisin A, trypsin, phytin, and type V collagenase used in Test Example 7 were used as other proteases. A group supplemented with none of these proteases was used as a control group.

In order to equalize conditions for the activity of the nattokinase and for the activities of various proteases described above, the activities (FLV) of these various proteases were adjusted to 100 by the calibration curve method in the same way as in Test Example 15.

100 mL of artificial seawater (Daigo's artificial seawater SP, manufactured by Nihon Pharmaceutical Co., Ltd.) was added to each 200-mL beaker. The solutions of various proteases prepared above were each mixed therewith. One piece (approximately 20 g) of *Aurelia aurita* cut into 3 cm square was dipped therein and incubated at 37° C. The jellyfish block residues in each solution left standing without stirring were sampled at each predetermined time point, and its mass was measured. The residual percentage (% by mass) with respect to the mass of the *Aurelia aurita* added was calculated. All the *Aurelia aurita* block decomposition tests were each conducted three times under the same conditions to confirm reproducibility.

Figure 16A:
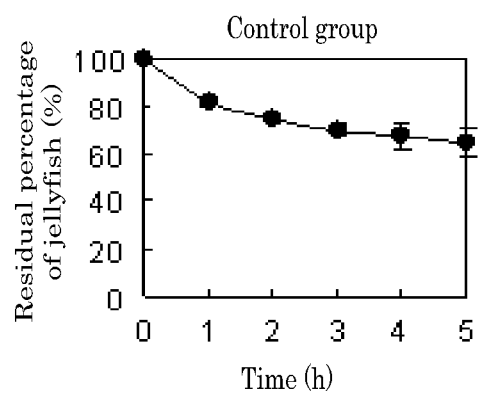
FIG. 16A is a diagram showing results of a control group in Test Example 15, wherein *Aurelia aurita* was dipped in artificial seawater. The ordinate denotes the residual percentage of jellyfish (%). The abscissa denotes treatment time (h).
Figure 16B:
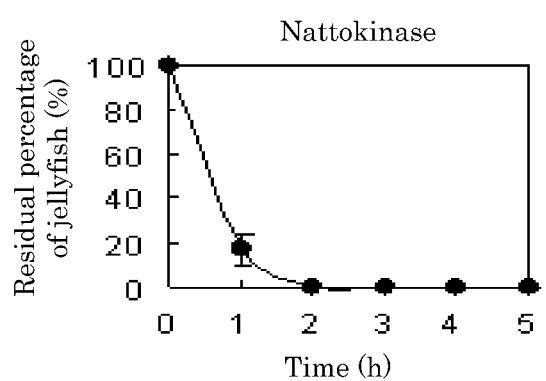
FIG. 16B is a diagram showing change in jellyfish mass caused by the decomposition of *Aurelia aurita* with nattokinase in Test Example 15. The ordinate denotes the residual percentage of jellyfish (%). The abscissa denotes treatment time (h).
Figure 16C:
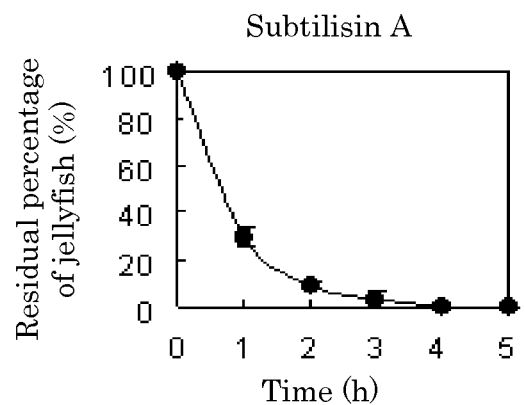
FIG. 16C is a diagram showing change in jellyfish mass caused by the decomposition of *Aurelia aurita* with subtilisin A in Test Example 15. The ordinate denotes the residual percentage of jellyfish (%). The abscissa denotes treatment time (h).
Figure 16D:
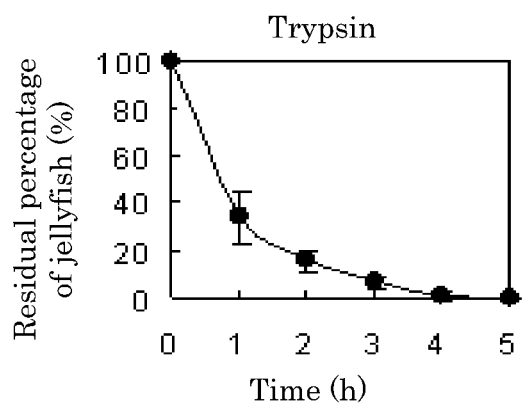
FIG. 16D is a diagram showing change in jellyfish mass caused by the decomposition of *Aurelia aurita* with trypsin in Test Example 15. The ordinate denotes the residual percentage of jellyfish (%). The abscissa denotes treatment time (h).
Figure 16E:
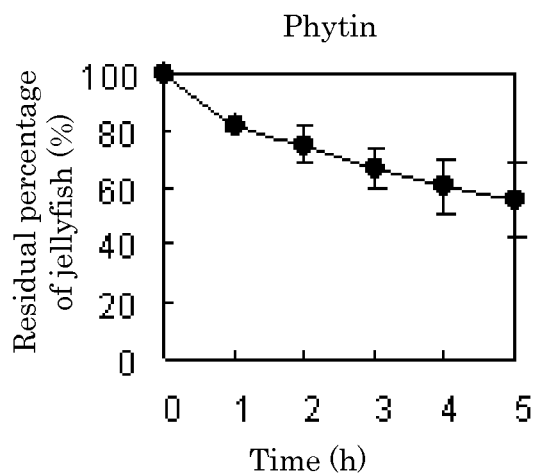
FIG. 16E is a diagram showing change in jellyfish mass caused by the decomposition of *Aurelia aurita* with phytin in Test Example 15. The ordinate denotes the residual percentage of jellyfish (%). The abscissa denotes treatment time (h).
Figure 16F:
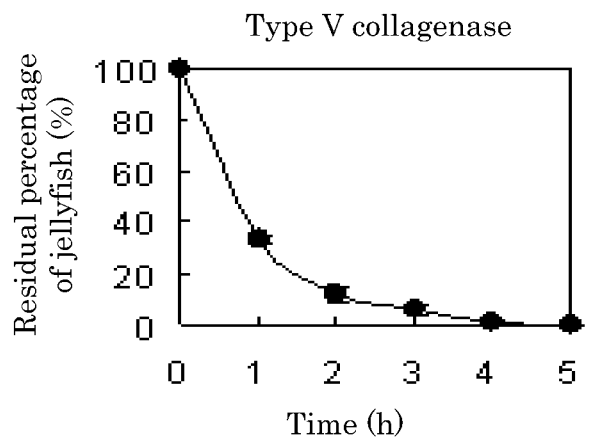
FIG. 16F is a diagram showing change in jellyfish mass caused by the decomposition of *Aurelia aurita* with type V collagenase in Test Example 15. The ordinate denotes the residual percentage of jellyfish (%). The abscissa denotes treatment time (h).

The results are shown in FIGS. 16A to 16F. In the control group merely dipped in artificial seawater, approximately 65% by mass of tissues remained without being lysed even after a lapse of 5 hours (FIG. 16A). By contrast, as for the nattokinase, approximately 20% residues were observed after 1 hour into the dipping, and the *Aurelia aurita* completely disappeared after 2 hours thereinto (FIG. 16B). As for the subtilisin A and the trypsin, which belong to the same serine protease family as in the nattokinase, 10% to 20% of the *Aurelia aurita* remained unlysed even after a lapse of 2 hours (FIGS. 16C and 16D). The plant-derived cysteine protease phytin, as in the control group, was hardly able to reduce the *Aurelia aurita* (FIG. 16E). The complete lysis of the *Aurelia aurita* was observed in the type V collagenase test group after a lapse of 5 hours (FIG. 16F).

These results demonstrated that among proteases, the nattokinase exhibits excellent decomposing activity against jellyfish.

Test Example 16

Study on Nattokinase-Mediated Inactivation of *Carybdea rastoni Haacke* Toxin Protein

*Carybdea rastoni Haacke* was collected in the coast of Kanagawa, Japan, immediately put into a vinyl bag, and frozen in dry ice. Then, the jellyfish individuals were brought to a laboratory and stored at −80° C. until subjected to the experiment. In order to obtain the *Carybdea rastoni Haacke* toxin, the jellyfish tentacle portion was thawed, then placed in a plastic container, and ultrasonically disrupted under ice cooling. The resulting product was used as a *Carybdea rastoni Haacke* toxin solution (hereinafter, also referred to as "CrTXs").

Plastic containers were used as all containers for tests shown below in order to prevent the irreversible adsorption of the toxin solution to glass containers.
—Method for Calculating Rate of Hemolysis—

8 µL of sheep erythrocytes (manufactured by Nippon Bio-Supp. Center) was suspended in 1 mL of PBS(+) (phosphate-buffered saline containing calcium and magnesium). To this suspension, an arbitrary amount of the *Carybdea rastoni Haacke* toxin solution (CrTXs) was added and mixed. This mixture was left at room temperature for 4 hours and then centrifuged at 3,000×g for 2 minutes. The absorbance of this supernatant was measured at a wavelength of 550 nm and used as a "test value".

Also, 8 µL of sheep erythrocytes was mixed with a 100-fold diluted lysis buffer solution (6% by mass of sodium dodecyl sulfate and 7% by mass of Triton X-100 solution). This mixture was left at room temperature for 4 hours and then centrifuged at 3,000×g for 2 minutes. The absorbance of this supernatant was measured at a wavelength of 550 nm. The rate of hemolysis at this absorbance was defined as 100% and used as a "control value".

The rate of hemolysis (%) was evaluated according to the following equation 3 from the test value and the control value thus determined:

Rate of hemolysis (%)=(Test value/Control value)×100 (equation 3)

Study on Influence of Nattokinase on Erythrocyte Hemolysis

The nattokinase prepared in Test Example 15 was used as nattokinase. Its enzyme activity (FLV) was calculated in the same way as in Test Example 3 and thereby confirmed to be 5,563 except that the nattokinase prepared in Test Example 15 was used instead of the culture supernatant of Test Example 3. This nattokinase was diluted to 5% by volume with PBS(+) (phosphate-buffered saline containing calcium and magnesium) and used in a test shown below.

The rate of hemolysis was calculated according to the equation 3 in the same way as in the method for calculating the rate of hemolysis except that 50 µL (5% by volume with respect to the *Carybdea rastoni Haacke* toxin solution) of the diluted nattokinase was added instead of the *Carybdea rastoni Haacke* toxin solution (CrTXs) for the calculation of the test value.

Figure 17:
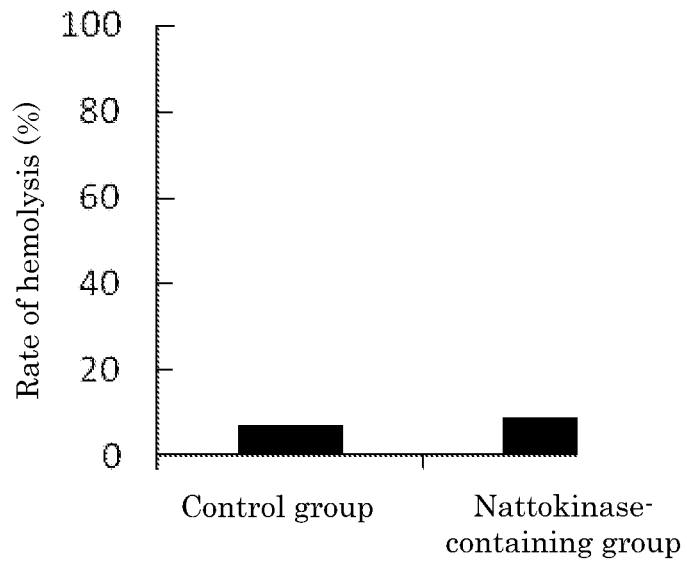
FIG. 17 is a diagram showing the relationship between the concentration of nattokinase and the rate of hemolysis of sheep erythrocytes in Test Example 16. The ordinate denotes the rate of hemolysis (%).

The results are shown in FIG. 17. The rate of hemolysis of sheep erythrocytes was 9.0% in the nattokinase-containing group. The rate of hemolysis was 7.1% in the control group containing no nattokinase. In this context, the enzyme activity (FLV) was 278.15.

This result demonstrated that 5% by volume of the nattokinase, i.e., having enzyme activity (FLV) of 278 or less does not cause the hemolysis of sheep erythrocytes.

Study on Influence of *Carybdea rastoni Haacke* Toxin on Erythrocyte Hemolysis

The *Carybdea rastoni Haacke* toxin was studied for its influence on erythrocyte hemolysis in the same way as in the method for calculating the rate of hemolysis. In this study, a *Carybdea rastoni Haacke* toxin solution (CrTXs) was added at each volume of 1 µL, 2 µL, 5 µL, 10 µL, 50 µL, and 100 µL.

Figures 18, 19:
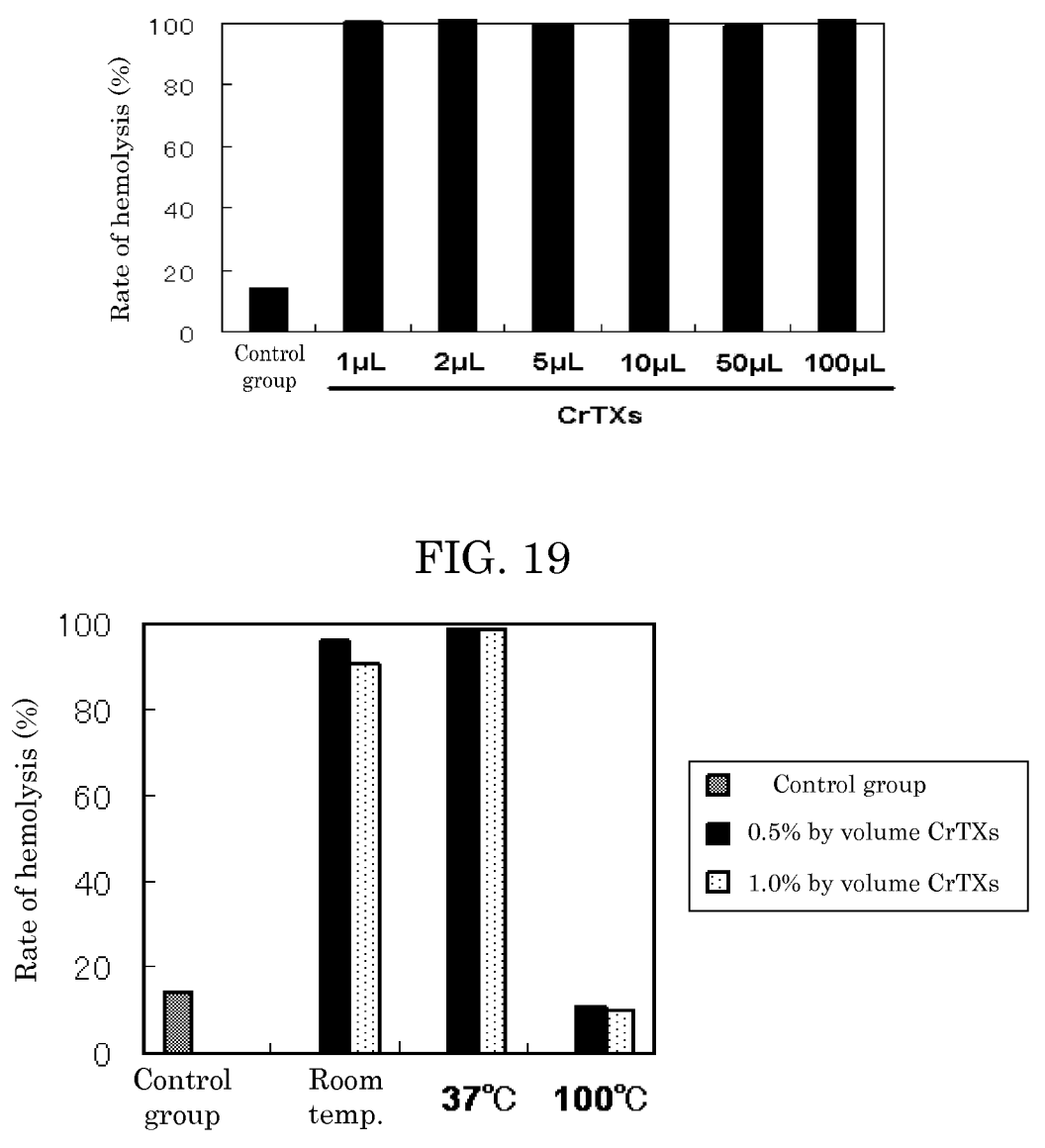

The results are shown in FIG. 18. As seen from the results of FIG. 18, the rate of hemolysis was 14.3% in the control group containing no *Carybdea rastoni Haacke* toxin solution (CrTXs), whereas the rate of hemolysis was found to be 100% in all the test groups supplemented with the *Carybdea rastoni Haacke* toxin solution (CrTXs).

The morphology of erythrocytes was not observed even under microscopic observation, suggesting that the erythrocytes were hemolyzed by the *Carybdea rastoni Haacke* toxin. Provided that the *Carybdea rastoni Haacke* toxin solution (CrTXs) was added in an amount of 0.1% by volume (1 µL), a longer time was required for complete hemolysis, compared with the other test groups.

Study on Thermal Stability of *Carybdea rastoni Haacke* Toxin

Next, the *Carybdea rastoni Haacke* toxin was studied for its thermal stability in the same way as in the method for calculating the rate of hemolysis.

The *Carybdea rastoni Haacke* toxin solution used in this test was the *Carybdea rastoni Haacke* toxin solution (CrTXs) left under each condition of room temperature (25° C.) for 30 minutes, 37° C. for 30 minutes, and 100° C. for 5 minutes. Each solution was added in an amount of 0.5% by volume (5 µL) or 1.0% by volume (10 µL).

The results are shown in FIG. 19 and Table 8 below. As seen from these results, the rate of hemolysis was 14.0% in the control group containing no *Carybdea rastoni Haacke* toxin solution (CrTXs).

The rate of hemolysis was shown to be 90% or more in the test group in which the *Carybdea rastoni Haacke* toxin solution (CrTXs) was left at room temperature or 37° C. for 30 minutes, demonstrating that heating for 30 minutes under these temperature conditions does not inactivate the *Carybdea rastoni Haacke* toxin.

By contrast, in the case of the test group in which the *Carybdea rastoni Haacke* toxin solution (CrTXs) was heated at 100° C. for 5 minutes, the rate of hemolysis was shown to be 11.0% or less in all the *Carybdea rastoni Haacke* toxin solutions (CrTXs) added at the volumes, suggesting that the *Carybdea rastoni Haacke* toxin was denatured by this heating and thereby inactivated.

TABLE 8

| Condition for heat treatment of CrTXs | | Untreated | Room temperature (25° C.), 30 min | 37° C., 30 min | 100° C., 5 min |
|---|---|---|---|---|---|
| Control group | | 14.0% | — | — | — |
| Test group | 0.5 vol % CrTXs added | — | 96.1% | 98.8% | 11.0% |
| | 1.0 vol % CrTXs added | — | 90.5% | 98.8% | 9.7% |

Study on Amount of Nattokinase that Inactivates *Carybdea rastoni Haacke* Toxin Protein In the method for calculating the rate of hemolysis, the *Carybdea rastoni Haacke* toxin solution (CrTXs) was added in an amount of 0.5% by volume (5 μL) and further mixed with the nattokinase at each volume of 0.1% by volume (1 μL), 0.5% by volume (5 μL), 1.0% by volume (10 μL), and 2.0% by volume (20 μL), followed by reaction at 37° C. for 30 minutes.

A group supplemented with neither the *Carybdea rastoni Haacke* toxin solution (CrTXs) nor the nattokinase was used as a control group.

Figure 20:
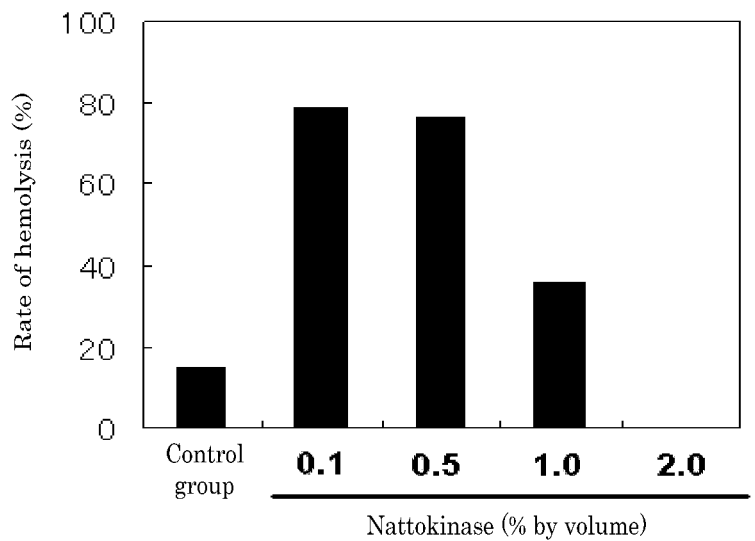
FIG. 20 is a diagram showing the ability of nattokinase to decompose the *Carybdea rastoni Haacke* toxin in Test Example 16. The ordinate denotes the rate of hemolysis (%).

The results are shown in FIG. 20 and Table 9 below. The results of FIG. 20 and Table 9 demonstrated that the *Carybdea rastoni Haacke* toxin solution can be left and thereby substantially completely inactivated at the constant temperature of 37° C. for 30 minutes under conditions involving a nattokinase amount of 2.0% by volume or more, i.e., enzyme activity (FLV) of 111 or more against casein as a substrate.

TABLE 9

| | CrTXs (% by volume) | Nattokinase (% by volume) | Rate of hemolysis (%) |
|---|---|---|---|
| Control group | 0 | 0 | 14.4% |
| Test group | 5 | 0.1 | 78.5% |
| | 5 | 0.5 | 76.4% |
| | 5 | 1.0 | 35.6% |
| | 5 | 2.0 | 0.2% |

Test Example 17

Study on Inactivation of *Carybdea rastoni Haacke* Toxin Protein by Various Proteases Nattokinase, subtilisin A, trypsin, phytin, and type V collagenase used as proteases in this test were prepared by the calibration curve method in the same way as in Test Example 15 so that their respective enzyme activities (FLV) were 111.

In the method for calculating the rate of hemolysis, the *Carybdea rastoni Haacke* toxin solution (CrTXs) was added in an amount of 2.0% by volume. In addition, the activities (FLV) of these various proteases were adjusted to 111 by the calibration curve method. Then, the solution and each protease were reacted at 37° C. for 30 minutes.

A group supplemented with neither the *Carybdea rastoni Haacke* toxin solution (CrTXs) nor the nattokinase was used as a control group.

Figure 21:
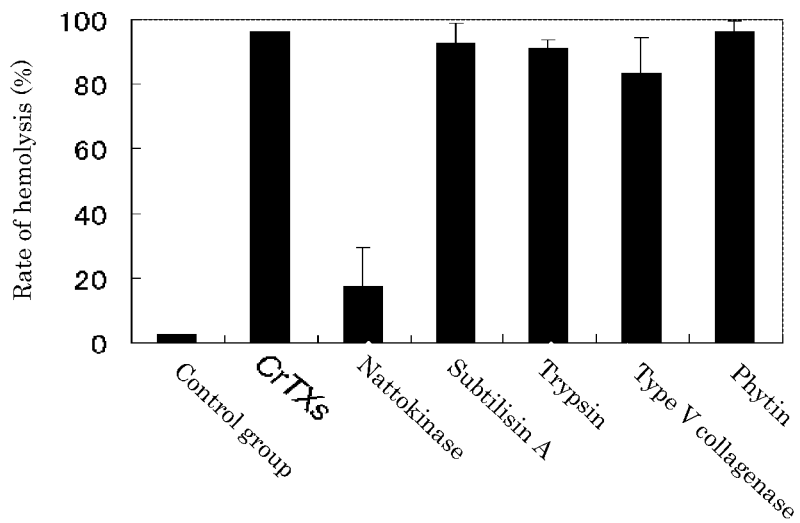
FIG. 21 is a diagram showing the ability of various enzymes to decompose the *Carybdea rastoni Haacke* toxin in Test Example 17. The ordinate denotes the rate of hemolysis (%).

The results are shown in FIG. 21 and Table 10 below. As seen from these results, use of the proteases (subtilisin A, trypsin, type V collagenase, and phytin) other than the nattokinase hardly inactivated the *Carybdea rastoni Haacke* toxin. By contrast, use of the nattokinase was shown to significantly inactivate the *Carybdea rastoni Haacke* toxin, with the low rate of hemolysis.

This demonstrated that among proteases, the nattokinase has the higher ability to decompose the *Carybdea rastoni Haacke* toxin under conditions involving the same enzyme activity values with casein decomposition as an index.

TABLE 10

| Addition of CrTXs | Type of protease | Rate of hemolysis (%) |
|---|---|---|
| − | − | 2.7 |
| + | − | 96.1 |
| + | Nattokinase | 17.3 |
| + | Subtilisin A | 92.5 |
| + | Trypsin | 91.0 |
| + | Type V collagenase | 83.4 |
| + | Phytin | 96.5 |

INDUSTRIAL APPLICABILITY

The microorganism belonging to the genus *Bacillus* of the present invention can efficiently produce a thrombolytic enzyme and as such, can be used preferably in the method for treating waste according to the present invention.

The method for treating waste can treat the waste conveniently, rapidly, and completely without requiring a huge place and can inexpensively reduce the volume of the waste by the treatment without requiring a great deal of thermal energy or electric energy, while the method can prevent the generation of foul odor during the treatment and further offers the treated waste with high safety. Accordingly, the method for treating waste can be used preferably in the treatment of waste containing various proteins and can be used particularly preferably in seaside industrial facilities such as power plants, the treatment of bycatch marine waste in the fishing industry or the like, and the treatment of marine industrial waste such as freshwater organism waste.

Accession Number
NITE BP-680

What is claimed is:

1. A method for treating waste, comprising:
   (a) contacting the waste with an amount of a thrombolytic enzyme effective for decomposing the waste, and
   (b) decomposing the enzyme contacted waste for a period of time and temperature sufficient therefor, wherein the thrombolytic enzyme is produced by a *Bacillus subtilis* 104-1-3-1 strain (Accession No: NITE BP-680); wherein the time of the decomposing is 5 minutes or longer and within 2 hours;
   wherein the temperature of the decomposing is 40° C. to 53° C.;
   and
   wherein the waste is jellyfish, fishery products, plankton, a jellyfish- or puffer-toxin, or any combination thereof.

2. The method for treating waste according to claim 1, wherein the thrombolytic enzyme is a nattokinase.

3. The method for treating waste according to claim 1, wherein the thrombolytic enzyme is a thrombolytic enzyme obtained by: mixing the *Bacillus subtilis* 104-1-3-1 strain (Accession No: NITE BP-680) with a proteinaceous raw material; fermenting the proteinaceous raw material with the *Bacillus subtilis* 104-1-3-1 strain (Accession No: NITE BP-680) thereby providing a grown fermentation culture containing the thrombolytic enzyme; and separating the thrombolytic enzyme from the grown fermentation culture obtained in the fermenting.

4. The method for treating waste according to claim 1, wherein the enzyme is produced by a carrier-immobilized *Bacillus subtilis* 104-1-3-1 strain (Accession No: NITE BP-680).

5. A method for treating waste, comprising:
   (a) contacting the waste with an effective amount of a *Bacillus subtilis* 104-1-3-1 strain (Accession No: NITE BP-680) that produces a thrombolytic enzyme,
   (b) decomposing the *B. subtilis*-contacted waste for a period of time and temperature sufficient therefor, wherein the thrombolytic enzyme produced by the *B. subtilis* decomposes the waste, wherein the time of the decomposing is 5 minutes or longer and within 2 hours, wherein the temperature of the decomposing is 40° C. to 53° C., and wherein the waste is jellyfish, fishery products, plankton, a jellyfish- or puffer-toxin, or any combination thereof.

6. The method for treating waste according to claim 5, wherein the *Bacillus subtilis* 104-1-3-1 strain (Accession No: NITE BP-680) is immobilized on a carrier.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1

```
agccatccgt cgatcatgga                                              20
```

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

```
taaaattccc gatattggtt                                              20
```

<210> SEQ ID NO 3
<211> LENGTH: 381
<212> TYPE: PRT
<213> ORGANISM: Bacillus Subtilis
<220> FEATURE:
<221> NAME/KEY: nattokinase (NITE P-680)
<222> LOCATION: (1)..(381)

<400> SEQUENCE: 3

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Ser Ser Thr Glu Lys Lys Tyr Ile Val Gly Phe Lys Gln Thr Met Ser
        35                  40                  45

Ala Met Ser Ser Ala Lys Lys Lys Asp Val Ile Ser Glu Lys Gly Gly
    50                  55                  60

Lys Val Gln Lys Gln Phe Lys Tyr Val Asn Ala Ala Ala Thr Leu
65                  70                  75                  80

Asp Glu Lys Ala Val Lys Glu Leu Lys Lys Asp Pro Ser Val Ala Tyr
                85                  90                  95

Val Glu Glu Asp His Ile Ala His Gly Tyr Ala Gln Ser Val Pro Tyr
            100                 105                 110

Gly Ile Ser Gln Ile Lys Ala Pro Ala Leu His Ser Gln Gly Tyr Thr
        115                 120                 125

Gly Ser Asn Val Lys Val Ala Val Ile Asp Ser Gly Ile Asp Ser Ser
    130                 135                 140

His Pro Asp Leu Asn Val Arg Gly Gly Ala Ser Phe Val Pro Ser Glu
145                 150                 155                 160

Thr Asn Pro Tyr Gln Asp Gly Ser Ser His Gly Thr His Val Ala Gly
                165                 170                 175

Thr Ile Ala Ala Leu Asn Asn Ser Ile Gly Val Leu Gly Val Ala Pro
            180                 185                 190

Ser Ala Ser Leu Tyr Ala Val Lys Val Leu Asp Ser Thr Gly Ser Gly
        195                 200                 205

Gln Tyr Ser Trp Ile Ile Asn Gly Ile Glu Trp Ala Ile Ser Asn Asn
    210                 215                 220

Met Asp Val Ile Asn Met Ser Leu Gly Gly Pro Thr Gly Ser Thr Ala
225                 230                 235                 240

Leu Lys Thr Val Val Asp Lys Ala Val Ser Ser Gly Ile Val Val Ala
                245                 250                 255

Ala Ala Ala Gly Asn Glu Gly Ser Ser Gly Ser Thr Ser Thr Val Gly
            260                 265                 270

Tyr Pro Ala Lys Tyr Pro Ser Thr Ile Ala Val Gly Ala Val Asn Ser
        275                 280                 285
```

-continued

```
Ser Asn Gln Arg Ala Ser Phe Ser Ser Val Gly Ser Glu Leu Asp Val
    290                 295             300

Met Ala Pro Gly Val Ser Ile Gln Ser Thr Leu Pro Gly Gly Thr Tyr
305                 310             315                 320

Gly Ala Tyr Asn Gly Thr Ser Met Ala Thr Pro His Val Ala Gly Ala
                325             330                 335

Ala Ala Leu Ile Leu Ser Lys His Pro Thr Trp Thr Asn Ala Gln Val
            340             345             350

Arg Asp Arg Leu Glu Ser Thr Ala Thr Tyr Leu Gly Asn Ser Phe Tyr
        355             360             365

Tyr Gly Lys Gly Leu Ile Asn Val Gln Ala Ala Ala Gln
    370             375             380
```